(12) United States Patent
Blood et al.

(10) Patent No.: US 9,181,361 B2
(45) Date of Patent: Nov. 10, 2015

(54) SYSTEMS AND METHODS FOR RECOVERING HYDROCARBONS FROM A POLYOLEFIN PURGE GAS PRODUCT

(75) Inventors: Mark W. Blood, Hurricane, WV (US); Randall L. Force, Charleston, WV (US); Theodore D. Duncan, Elkview, WV (US); George W. Schwarz, Jr., Charleston, WV (US); Daniel W. Mosser, Hurricane, WV (US); Donald A. Fischer, Cross Lane, WV (US); Robert D. Olson, Charleston, WV (US); James Leland Swecker, II, Clendenin, WV (US); Cloid Russell Smith, III, Charleston, WV (US)

(73) Assignee: Univation Technologies, LLC, Houston, TX (US)

( * ) Notice: Subject to any disclaimer, the term of this patent is extended or adjusted under 35 U.S.C. 154(b) by 269 days.

(21) Appl. No.: 13/992,465

(22) PCT Filed: Dec. 13, 2011

(86) PCT No.: PCT/US2011/064525
§ 371 (c)(1),
(2), (4) Date: Jul. 24, 2013

(87) PCT Pub. No.: WO2012/082674
PCT Pub. Date: Jun. 21, 2012

(65) Prior Publication Data
US 2013/0291720 A1 Nov. 7, 2013

Related U.S. Application Data

(60) Provisional application No. 61/424,300, filed on Dec. 17, 2010.

(51) Int. Cl.
*B01D 53/00* (2006.01)
*C08F 6/00* (2006.01)
(Continued)

(52) U.S. Cl.
CPC .............. *C08F 6/005* (2013.01); *B01D 53/00* (2013.01); *B01D 53/002* (2013.01);
(Continued)

(58) Field of Classification Search
CPC ............ B01D 53/00; C07C 7/005; C08F 6/00
USPC ........................................................ 95/39
See application file for complete search history.

(56) References Cited

U.S. PATENT DOCUMENTS 4,230,437 A    10/1980  Bellinger et al.
4,505,647 A     3/1985  Alloca et al.
(Continued)

FOREIGN PATENT DOCUMENTS

JP        2003144827         5/2003

OTHER PUBLICATIONS

Japanese Notice of Reasons of Refusal for related JP Patent Application No. 2013-544663, filed Jun. 14, 2013, mailed on May 19, 2015 (4 pgs).

*Primary Examiner* — Robert A Hopkins
(74) *Attorney, Agent, or Firm* — Brooks, Cameron & Huebsch, PLLC

(57) ABSTRACT

Provided are systems and methods for separating a purge gas recovered from a polyethylene product. The method includes recovering a polyethylene product containing one or more volatile hydrocarbons from a polymerization reactor and contacting the polyethylene product with a purge gas to remove at least a portion of the volatile hydrocarbons to produce a polymer product having a reduced concentration of volatile hydrocarbons and a purge gas product enriched in volatile hydrocarbons. The purge gas product is compressed to a pressure of 2,500 kPaa to 10,000 kPaa, and is then cooled and separated into at least a first product, a second product, and a third product. A portion of one or more of the first, second, or third products is then recycled as a purge gas, to the polymerization reactor, or to the purge gas product enriched in volatile hydrocarbons prior to compression, respectively.

20 Claims, 4 Drawing Sheets

(51) Int. Cl.
  *B01D 53/14* (2006.01)
  *C07C 7/00* (2006.01)
  *C08J 11/02* (2006.01)
  *F25J 3/08* (2006.01)
  *F25J 3/06* (2006.01)

(52) U.S. Cl.
  CPC ........... *B01D 53/1487* (2013.01); *C07C 7/005* (2013.01); *C08F 6/00* (2013.01); *C08J 11/02* (2013.01); *F25J 3/062* (2013.01); *F25J 3/064* (2013.01); *F25J 3/066* (2013.01); *F25J 3/08* (2013.01); *B01D 2256/10* (2013.01); *B01D 2256/24* (2013.01); *B01D 2257/102* (2013.01); *B01D 2257/702* (2013.01); *B01D 2257/708* (2013.01); *B01J 2219/00006* (2013.01); *F25J 2210/12* (2013.01); *F25J 2220/02* (2013.01); *F25J 2230/30* (2013.01); *F25J 2235/60* (2013.01); *F25J 2260/42* (2013.01); *F25J 2260/60* (2013.01)

(56) References Cited

U.S. PATENT DOCUMENTS

| | | | |
|---|---|---|---|
| 4,618,310 A | | 10/1986 | Michelson |
| 5,016,447 A | | 5/1991 | Lane et al. |
| 5,095,712 A | | 3/1992 | Narreau |
| 5,139,399 A | | 8/1992 | Hood |
| 5,391,656 A | † | 2/1995 | Campbell |
| 5,741,350 A | * | 4/1998 | Rowles et al. ............ 95/42 |
| 6,576,043 B2 | * | 6/2003 | Zwilling et al. ........... 95/41 |
| 6,638,029 B2 | | 10/2003 | Kharsa |

\* cited by examiner
† cited by third party

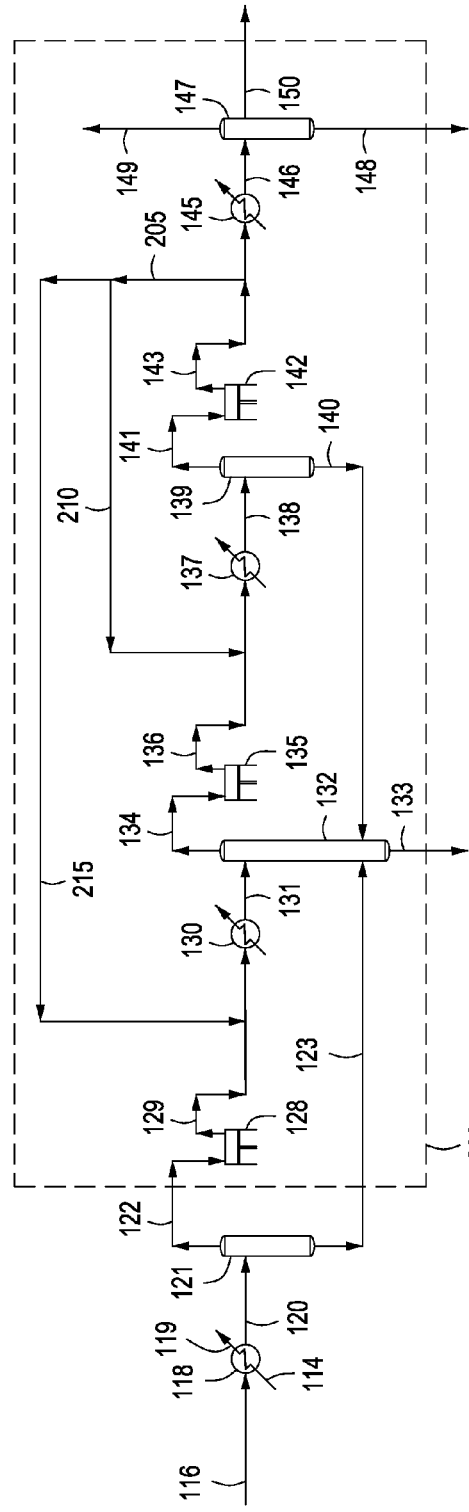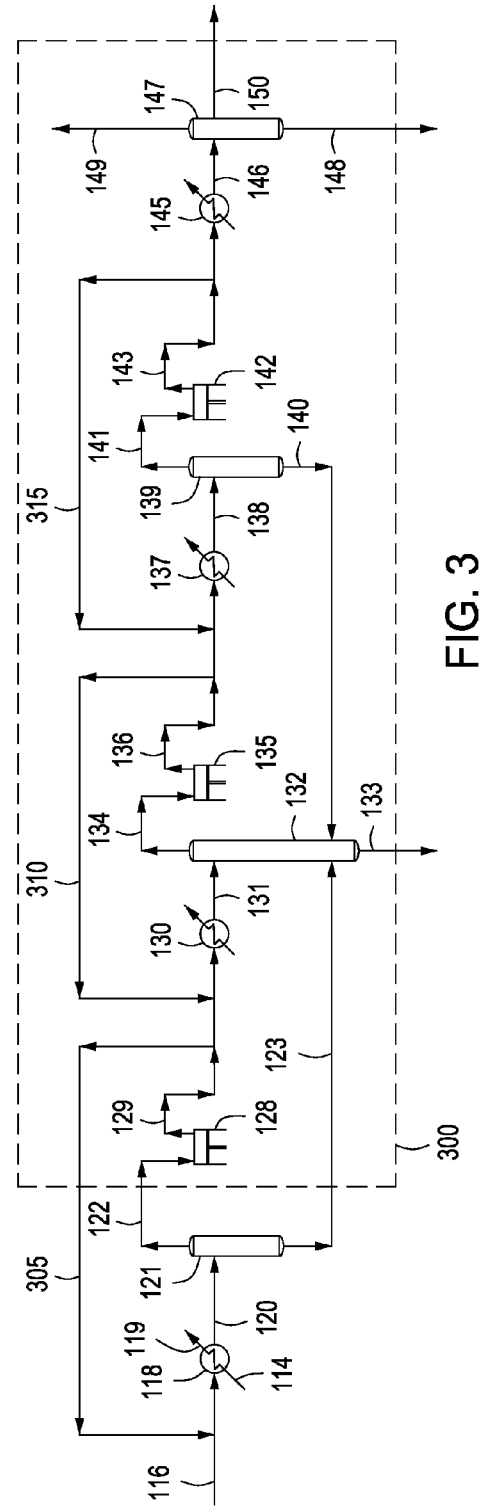

SYSTEMS AND METHODS FOR RECOVERING HYDROCARBONS FROM A POLYOLEFIN PURGE GAS PRODUCT

CROSS-REFERENCE TO RELATED APPLICATIONS

This application is a National Stage application under 35 U.S.C. §371 of International Application No. PCT/US2011/064525, filed Dec. 13, 2011, that claims the benefit of Ser. No. 61/424,300, filed Dec. 17, 2010, the disclosures of which are incorporated by reference in their entireties.

BACKGROUND

In gas-phase polymerization, a gaseous stream containing one or more monomers is passed through a fluidized bed under reactive conditions in the presence of a catalyst. A polymer product is withdrawn from the reactor while fresh monomer is introduced to the reactor. Residual gaseous and/or liquid components such as unreacted hydrocarbon monomer(s) and/or diluent(s) are usually absorbed in the polymer product. These volatile, unreacted monomers and/or diluents need to be removed from the polymerized particulates.

Typically the polymer product is introduced to a product separator or purge bin and contacted with a countercurrent flow of a purge gas such as nitrogen. The recovered purge gas product that includes the purge gas and volatile, unreacted monomers and/or diluents is either flared, used as fuel, or undergoes further processing to recover the valuable monomers and/or diluents. Current separation systems utilize membrane separation, adsorption materials, and/or pressure swing adsorption. While some of the valuable monomers and/or diluents are recovered, the remaining nitrogen purge gas must be flared or combusted as fuel because the concentration of monomers and/or diluents in the purge gas remains too high.

There is a need, therefore, for improved systems and methods for recovering hydrocarbons from a polymerization purge gas.

SUMMARY

Systems and methods for recovering hydrocarbons from a polyolefin purge gas product are provided. The method can include recovering a polyolefin product comprising one or more volatile hydrocarbons from a polymerization reactor and contacting the polyolefin product with a purge gas to remove at least a portion of the volatile hydrocarbons to produce a polyolefin product having a reduced concentration of volatile hydrocarbons and a purge gas product enriched in volatile hydrocarbons. The volatile hydrocarbons can include hydrogen, methane, one or more $C_2$-$C_{12}$ hydrocarbons, or any combination thereof. The purge gas product can be at a pressure of about 50 kPa to about 250 kPa. The method can also include compressing the purge gas product to a pressure of about 2,500 kPa to about 10,000 kPa. The method can also include cooling and separating the compressed purge gas product into at least a first product, a second product, and a third product. The method can also include recycling at least a portion of at least one of the first product as the purge gas, the second product to the polymerization reactor, and the third product to the purge gas product enriched in volatile hydrocarbons prior to compression.

The system for recovering hydrocarbons from a polyolefin purge gas product can include a purge bin, a compression system, a refrigeration system, and at least one recycle line. The purge bin can be adapted to receive a polyolefin product comprising one or more volatile hydrocarbons from a polymerization reactor. The polyolefin product can be contacted with a purge gas within the purge bin to remove at least a portion of the volatile hydrocarbons to produce a polyolefin product having a reduced concentration of volatile hydrocarbons and a purge gas product enriched in volatile hydrocarbons. The volatile hydrocarbons can include hydrogen, methane, one or more $C_2$-$C_{12}$ hydrocarbons, or any combination thereof. The purge gas product can be at a pressure of about 50 kPa to about 250 kPa. The compression system can be adapted to compress the purge gas product to a pressure of about 2,500 kPa to about 10,000 kPa. The refrigeration system can be adapted to cool and separate the compressed purge gas product into at least a first product, a second product, and a third product. The at least one recycle line can be adapted to recycle at least a portion of at least one of the first product as the purge gas, the second product to the polymerization reactor, and the third product to the purge gas product enriched in volatile hydrocarbons prior to compression.

In the method and system described herein the polyolefin product may comprise polyethylene homopolymers, polypropylene homopolymers, polyethylene copolymers, or polypropylene copolymers.

In the method and system described herein the refrigeration system may be an auto-refrigeration system.

BRIEF DESCRIPTION OF THE DRAWINGS

FIG. 2 depicts a schematic of an illustrative compression system for compressing a purge gas product recovered from a polymerization system.

FIG. 3 depicts a schematic of an illustrative compression system for compressing a purge gas product recovered from a polymerization system.

DETAILED DESCRIPTION

Figure 1:
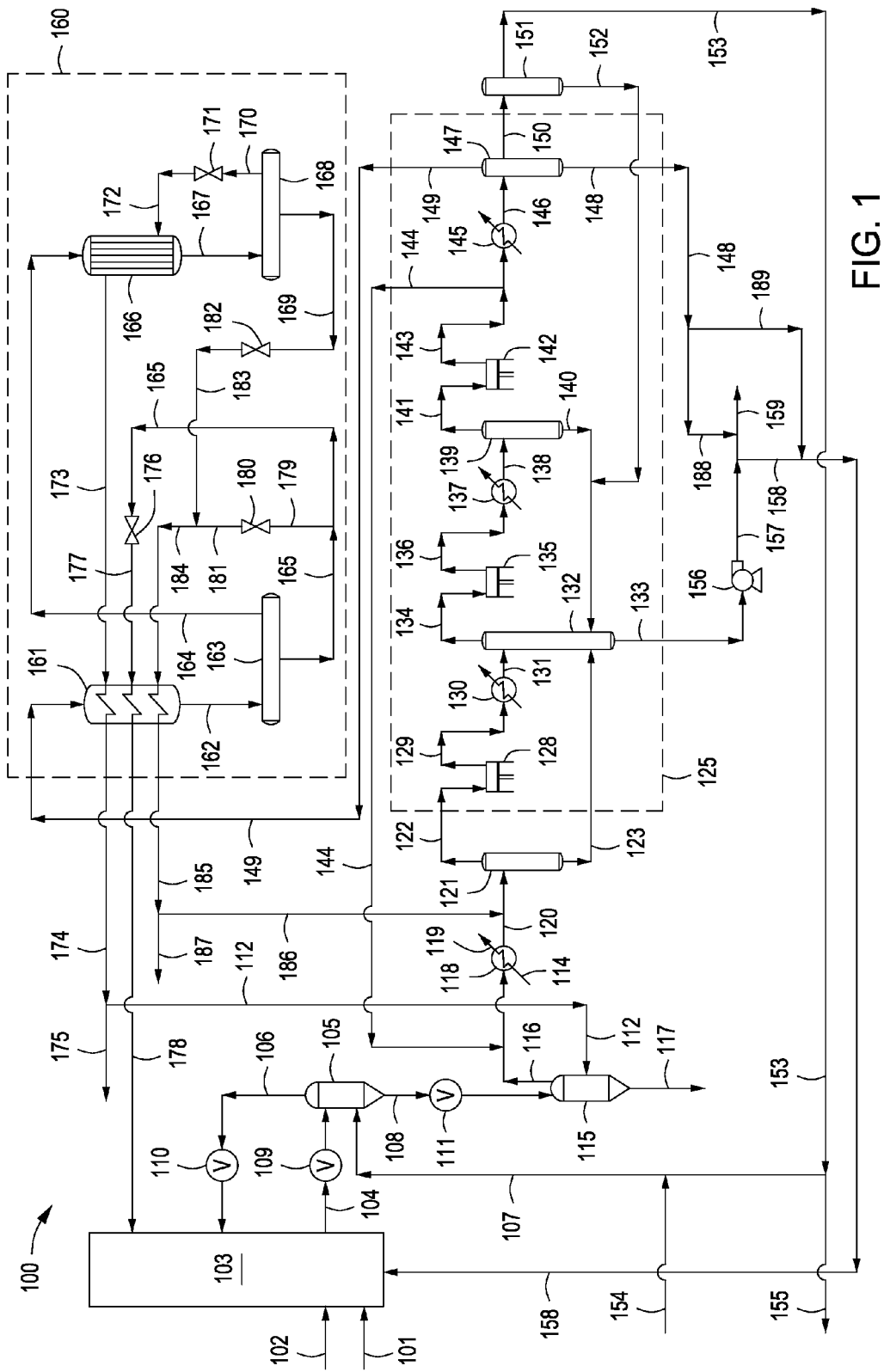
FIG. 1 depicts a schematic of an illustrative polymerization system for making polymer products and recovering volatiles therefrom.

FIG. 1 depicts a schematic of an illustrative polymerization system 100 for making one or more polymer products and recovering volatiles therefrom. A reactor feed via line 101 and a catalyst feed via line 102 can be introduced to a polymerization reactor 103 where the reactor feed can be polymerized to produce a polymer product. The polymer product via line 104 can be recovered from the polymerization reactor 103 and introduced to one or more product discharge systems 105. Within the product discharge system 105 a first portion of any volatiles contained in the polymer product via line 106 can be recovered therefrom and recycled to the reactor 103. A product discharge assist gas via line 107 can be introduced to the product discharge system 105 and the polymer product via line 108 can be transferred from the product discharge system 105 to one or more purge bins 115. The product discharge assist gas via line 107 can facilitate the conveyance or transport of the polymer product via line 108 from the product discharge system 105 to the purge bin 115. One or more flow control devices, e.g., valves, 109, 110, and 111, can be used to control the introduction of the polymer product via line 104 to the product discharge system 105, removal of the first portion of volatiles via line 106, and removal of the polymer product via line 108, respectively, from the product discharge system 105. The particular timing sequence of the flow control devices 109, 110, 111 can be accomplished by the use of conventional programmable controllers which are known in the art.

A purge gas via line 112 can be introduced to the purge bin 115 and can contact the polymer product within the purge bin 115 to separate at least a portion of any remaining volatiles from the polymer product. The purge gas and the separated volatiles or "purge gas product" via line 116 and the polymer product via line 117 can be recovered from the purge bin 115. The polymer product via line 117 can be introduced to a storage vessel, packaged and shipped as a final product, further processed into one or more products, e.g., processed into a film or other article and/or blended with one or more other polymers, etc., or any combination thereof. The purge gas product in line 116 can be processed to at least partially separate one or more of the various components therein.

Depending, at least in part, on the particular polymer product recovered via line 104 from the polymerization reactor 103, the composition of the purge gas product in line 116 can widely vary. The polymer product in line 104 can be or include any desirable polymer or combination of polymers. For example, the polymer product in line 104 can be or include one or more polyethylenes, polypropylenes, propylene copolymerized with ethylene, and the like. Preferably the polymer product includes polyethylene and/or polyethylene copolymers. The term "polyethylene" refers to a polymer having at least 50 wt % ethylene-derived units, or at least 70 wt %, or at least 80 wt %, or at least 90 wt %, or at least 95 wt %, or 100 wt % ethylene-derived units. The polyethylenes can thus be homopolymers or copolymers, including a terpolymer, having one or more other monomeric units, or any combination thereof. As such, the polymer product can include, for example, one or more other olefins) and/or α-olefin comonomer(s). Illustrative α-olefin comonomers can include, but are not limited to, those having from 3 to about 20 carbon atoms, such as $C_3$-$C_{20}$ α-olefins, $C_3$-$C_{12}$ α-olefins, or $C_3$-$C_8$ α-olefins. Suitable α-olefin comonomers can be linear or branched or can include two unsaturated carbon-carbon bonds (dienes). Two or more comonomers can be used. Examples of suitable comonomers can include, but are not limited to, linear $C_3$-$C_{12}$ α-olefins and α-olefins having one or more $C_1$-$C_3$ alkyl branches or an aryl group.

The various volatile hydrocarbons and/or other components contained in the purge gas product in line 116 can include, but are not limited to, hydrogen, the purge gas (e.g. nitrogen), methane, any olefin monomer or combination of olefins including substituted and unsubstituted alkenes having two to 12 carbon atoms, such as ethylene, propylene, 1-butene, 1-pentene, 1-hexene, 1-heptene, 1-octene, 4-methylpent-1-ene, 1-decene, 1-dodecene, 1-hexadecene, and the like. The purge gas product in line 116 can also include one or more modifying components used in the polymerization of the olefins) such as one or more inert hydrocarbons used as a solvent, slurry diluent, or gas phase induced condensing agents (ICA). Illustrative inert hydrocarbons can include, but are not limited to, ethane, propane, butane, pentane, hexane, isomers thereof, derivatives thereof, or any combination thereof. The purge gas product can also include catalytic components such as alkylaluminum compounds, such as triethylaluminum (TEAL), aluminoxanes such as methylaluminoxane (MAO), tetraisobutyldialuminoxane (TIBAO), or any combination thereof.

The purge gas in line 112 can include any fluid or combination of fluids suitable for purging, i.e. separating, at least a portion of the volatiles in the polymer product to produce the polymer product via line 117 having a reduced concentration of volatiles relative to the polymer product in line 104. Illustrative purge gases can include, but are not limited to, nitrogen, argon, carbon monoxide, carbon dioxide, hydrocarbons such as ethylene and/or ethane, or any combination thereof. In at least one example, the purge gas product in line 116 includes a mixture of the purge gas, e.g., nitrogen, and the volatiles removed from the polymer product include ethylene, one or more ICAs, and one or more α-olefin comonomers such as butene, hexene, and/or octene.

The purge gas product in line 116 can be at a pressure ranging from about atmospheric pressure (about 101 kPa) to about 300 kPa, all pressures herein are absolute pressure unless otherwise noted. For example, the pressure of the purge gas in line 116 can range from a low of about 101 kPa, about 105 kPa, or about 110 kPa to a high of about 150 kPa, about 200 kPa, or about 250 kPa. In another example, the purge gas product in line 116 can be under a vacuum, i.e. below atmospheric pressure. For example, the purge gas product in line 116 can be at a pressure ranging from a low of about 40 kPa, about 50 kPa, or about 60 kPa to a high of about 70 kPa, about 80 kPa, about 90 kPa, or about 100 kPa.

The purge gas product in line 116 can be at a temperature ranging from about room or atmospheric temperature (about 25° C.) to about 120° C. For example, the temperature of the purge gas product in line 116 can range from a low of about 30° C., about 40° C., or about 50° C. to a high of about 80° C., about 90° C., about 100° C., or about 110° C.

Depending on the temperature of the purge gas product in line 116, the purge gas product via line 116 can be introduced to one or more heat exchangers (one is shown 118), which can reduce the temperature thereof. For example, the purge gas product via line 116 and a heat transfer medium via line 114 can be introduced to the heat exchanger 118 where heat can be indirectly transferred from the purge gas to the heat transfer medium within the heat exchanger 118 to produce a cooled purge gas product via line 120 and a warmed heat transfer medium via line 119. The purge gas product in line 120 can be at a temperature of from about 20° C. to about 60° C. For example, the temperature of the purge gas product in line 120 can be less than about 55° C., less than about 45° C., less than about 40° C., less than about 35° C., or less than about 30° C. Any suitable heat transfer medium or combination of heat transfer mediums via line 114 can be introduced to the heat exchanger 118. Illustrative heat transfer mediums can include, but are not limited to, water, air, one or more hydrocarbons, nitrogen, argon, or any combination thereof. If a cooler temperature is desired, one or more refrigeration systems can be used to reduce the temperature of the purge gas product to less than about 30° C. For example, refrigerant systems can reduce the temperature of the purge gas product in line 120 to a temperature of about 15° C. or less, about 0° C. or less, about −5° C. or less, or about −15° C. or less. Illustrative refrigerants can include, for example, hydrocarbons.

The purge gas product via line 120 can be introduced to a separator 121, which can separate at least a portion of any condensed fluid from the purge gas product. The separated condensed fluid via line 123 and the purge gas product via line 122 can be recovered from the separator 121.

The purge gas product via line 122 can be introduced to a compression system 125 to produce a compressed purge gas product via line 149 and a recovered, condensed product via lines 133 and/or 148. The compressed purge gas product in line 149 can be at a pressure of about 2,500 kPa or more, about 2,700 kPa or more, about 2,900 kPa or more, about 3,200 kPa or more, about 3,500 kPa or more, about 3,700 kPa or more, about 3,900 kPa or more, about 4,100 kPa or more, about 4,300 kPa or more, about 4,500 kPa or more, about 5,000 kPa or more, about 7,000 kPa or more, about 8,000 kPa or more, about 9,000 kPa or more, or about 10,000 kPa or more. For example, the compressed purge gas product in line 149 can be at a pressure ranging from a low of about 2,500 kPa, about 2,700 kPa, about 3,100 kPa, about 3,500 kPa, about 4,000 kPa, or about 4,100 kPa to a high of about 5,000 kPa, about 7,000 kPa, about 9,000 kPa, or about 11,000 kPa. In another example, the compressed purge gas product in line 149 can be at a pressure of about 3,800 kPa to about 4,400 kPa, or about 4,000 kPa to about 5,000 kPa, or about 3,700 kPa to about 7,000 kPa, or about 4,000 kPa to about 4,700 kPa, or about 2,500 to about 10,000.

During compression of the purge gas product within the compression system 125 the temperature of the purge gas product can be maintained below a predetermined maximum temperature. The predetermined maximum temperature can be based, at least in part, on the particular make-up or composition of the purge gas product in line 116. For example, if the purge gas product includes catalytic components such as triethylaluminum (TEAL) and one or more olefins, the predetermined maximum temperature could be about 140° C. because, if the purge gas product is heated to higher temperatures, polymerization could be initiated within the compression system. Depending, at least in part, on the particular composition of the purge gas product, e.g., the presence of catalytic components and/or the concentration of catalytic component(s) in the purge gas product, the temperature of the purge gas product can be maintained below about 250° C., below about 225° C., below about 200° C., below about 175° C., below about 150° C., below about 140° C., below about 130° C., below about 120° C., below about 110° C., or below about 100° C., during compression thereof.

The purge gas product via line 116 can have a concentration of one or more catalytic components ranging from about 1 ppmw to about 500 ppmw. For example, the purge gas product in line 116 can have a concentration of one or more catalytic components ranging from a low of about 1 ppmw, about 10 ppmw, or about 25 ppmw to a high of about 100 ppmw, about 150 ppmw, about 200 ppmw, or about 250 ppmw. In another example, the purge bin 115 can produce a purge gas product free of or essentially free of catalytic components, e.g., less than about 1 ppmw, less than about 0.5 ppmw, or less than about 0.1 ppmw.

The purge gas product introduced via line 122 to the compression system 125 can be compressed in a plurality of compressors or compression stages. As shown in FIG. 1, the compression system 125 includes three compressors or compression stages 128, 135, and 142 serially arranged with respect to one another to produce the compressed purge gas product via line 149. In another example, the purge gas product introduced via line 122 to the compression system 125 can be compressed in two or more compressors or compression stages to produce the compressed purge gas product via line 149. Any number of compression stages can be used to produce the compressed purge gas product via line 149. For example, the compression system 125 can include two compressors, three compressors, four compressors, five compressors, six compressors, or seven compressors. Increasing the number of compressors or compression stages within the compression system 125 can reduce the temperature rise of the purge gas product through each compression stage.

The compressors 128, 135, 142 can compress the purge gas product at any desired pressure ratio, i.e. any desired ratio of the pressure of the purge gas product introduced to a particular compressor as compared to the pressure of the compressed purge gas product recovered from that compressor. As a specific example, a purge gas product at a pressure of about 110 kPa introduced via line 122 to the compressor 128 and compressed to a pressure of about 385 kPa would have a pressure ratio of about 1:3.5. The compressors 128, 135, 142 can compress the purge gas product at a pressure ratio ranging from a low of about 1:2, about 1:3, or about 1:4 to a high of about 1:5, about 1:6, about 1:7, about 1:8, about 1:9, or about 1:10. In another example, the compressors 128, 135, 142 can compress the purge gas product at a pressure ratio ranging from a low of about 1:2.5, about 1:2.7, about 1:3.0, about 1:3.1, or about 1:3.2 to a high of about 1:3.6, about 1:3.8, about 1:4.0, about 1:4.5, about 1:5, about 1:5.5, or about 1:6. In another example, the compressors 128, 135, 142 can compress the purge gas product at a pressure ratio of about 1:3.2 to about 1:3.6, about 1:3.1 to about 1:5, about 1:3.2 to about 1:4, about 1:3.4 to about 1:5, or about 1:3.0 to about 1:4. In another example, the compressors 128, 135, 142 can compress the purge gas product at a pressure ratio of about 1:3 to about 1:6, about 1:4 to about 1:9, about 1:5 to about 1:9, about 1:5 to about 1:8, about 1:6 to about 1:8, or about 1:4 to about 1:8. The particular pressure ratio within each compressor 128, 135, 142 can be based, at least in part, on the desired pressure of the compressed purge gas product produced via line 149, the particular components contained in the purge gas product in line 116, the type of compressor, the desired predetermined maximum temperature of the compressed purge gas after any particular compressor, or any combination thereof.

Compressor discharge temperature is directly related the pressure ratio of the product purge gas introduced to a particular compressor or compression stage and the compressed purge gas product recovered from the compressor. As the purge gas product is compressed within the first, second, and third compressors 128, 135, 142 to produce the compressed purge gas product via line 149, the partial pressure of monomers, e.g., ethylene, increases. As such, the potential for polymerization initiating when one or more catalytic components such as TEAL are present in the purge gas product can increase. Thus, controlling the maximum temperature of the compressed purge gas recovered from each compressor or compression stage 128, 135, 142 can be desirable as the pressure increases. As such, the pressure ratio at which the purge gas product is compressed within each compressor 128, 135, and 142 can be different from one another.

The first compressor 128 can compress the purge gas product introduced via line 122 at a pressure ratio equal to or greater than the second and third compressors 135, 142 compresses the purge gas product. For example, the first compressor 128 can compress the purge gas product introduced via line 122 thereto at a pressure ratio of at least 1:3, at least 1:3.5, at least 1:4, at least 1:4.5, or at least 1:5 and the second and third compressors can compress the purge gas product at a pressure ratio equal to or less than the first compressor 128. The first and second compressors 128, 135 can compress the purge gas product introduced via lines 122 and 134, respectively, at a pressure ratio equal to or greater than the third compressor 142 compresses the purge gas product introduced via line 141. As such, the pressure ratios at which the purge gas product is compressed within the first, second, and third compressors 128, 135, 142 can decrease as the purge gas product is compressed within the compression system 125.

The predetermined maximum temperature of each compressed purge gas product recovered from the compressors 128, 135, and 142 via lines 129, 136, and 143, respectively, can decrease as the pressure of the compressed purge gas product increases. In other words, the compressed purge gas product recovered via lines 129, 136, and 143 from each compressor 128, 135, 142, respectively, can have a different predetermined maximum temperature. The predetermined maximum temperature of the compressed purge gas product in line 129 can be equal to or greater than the predetermined maximum temperature of the purge gas product in line 136. Similarly, the predetermined maximum temperature of the compressed purge gas product in line 136 can be equal to or greater than the predetermined maximum temperature of the compressed purge gas product in line 143. For example, the predetermined maximum temperature of the compressed purge gas in line 129 can range from about 125° C. to about 150° C., the predetermined maximum temperature of the compressed purge gas inline 136 can range from about 115° C. to about 130° C., and the predetermined maximum temperature of the compressed purge gas in line 143 can range from about 105° C. to about 120° C. The particular predetermined maximum temperature for any particular compressed purge gas 129, 136, 143 can vary and can depend, at least in part, on the particular composition of the purge gas in line 116.

The compression system 125 can also include one or more heat exchangers and/or one or more separators that can cool and separate at least a portion of any condensed fluid from the compressed purge gas after one or more of the compression stages. As shown, the compression system 125 can include heat exchangers 130, 137, and 145 adapted to cool the compressed purge gas after each compression stage and separators 132, 139, and 147 that can separate at least a portion of any condensed fluid, if present, from the cooled compressed purge gas product recovered from the heat exchangers 130, 137, 145, respectively. The compressed purge gas product recovered via line 129 from the first compressor 128 can be cooled within the heat exchanger 130 to produce a cooled first compressed purge gas product via line 131. The cooled first compressed purge gas product via line 131 can be introduced to the separator 132 to recover at least a portion of any condensed fluid via line 133 and a purge gas product via line 134. The purge gas product via line 134 can be compressed within compressor 135 and recovered via line 136 as a second compressed purge gas product. The second compressed purge gas product via line 136 can be introduced to the heat exchanger 137 to produce a cooled second compressed purge gas product via line 138. The cooled second compressed purge gas product via line 138 can be introduced to the separator 139 to recover at least a portion of any condensed fluid via line 140 and a purge gas product via line 141. The purge gas product via line 141 can be introduced to the third or final compressor 142 (as shown) to produce a third or final compressed purge gas product via line 143. The third compressed purge gas product via line 143 can be introduced to heat exchanger 145 to produce a cooled third compressed purge gas product via line 146. The cooled third compressed purge gas product via line 146 can be introduced to the separator 147 to recover at least a portion of any condensed fluid via line 148 and the compressed purge gas product via line 149. Optionally, a portion of the compressed purge gas product via line 150 can be recovered from the separator 147 and introduced to another separator 151. The separator 151 can further separate at least a portion of any condensed fluid which can be recovered via line 152 therefrom and a purge gas product via line 153. The separator 151 can also be configured or adapted to act as a surge vessel. In other words, the separator 151 can be configured or adapted to accommodate fluctuations or changes in the amount of compressed purge gas product introduced thereto via line 150. The separator 151 can also be configured or adapted to accommodate fluctuations or changes in an amount of purge gas withdrawn via line 153 therefrom. The purge gas product via line 153 can be recycled as the product discharge assist gas via line 107 to the product discharge system 105. A make-up product discharge assist gas via line 154 can also be introduced to the purge gas product in line 107. In another example, all or a portion of the purge gas product in line 153 can be vented from the system 100, introduced to a flare system, introduced to a combustion device or system and combusted as fuel, or any combination thereof via line 155.

The heat exchangers 118, 130, and 137 can reduce the temperature of the compressed purge gas product prior to introduction to the first, second, and third compressors 128, 135, 142, respectively, a sufficient amount such that the temperature increase associated with the compression of the purge gas product, and as such the temperature of the compressed purge gas product recovered therefrom can be controlled. For example, the heat exchangers 118, 130, and 137 can reduce the temperature of the purge gas product introduced via lines 116, 129, and 136, respectively, such that the temperature of the purge gas product after each subsequent compression stage can be maintained below about 250° C., below about 200° C., below about 150° C., below about 140° C., below about 130° C., below about 120° C., below about 115° C., below about 110° C., below about 105° C., or below about 100° C.

The temperature of the cooled purge gas products recovered via lines 120, 131, and 138, and 146 from heat exchangers 118, 130, 137, and 145, respectively, can be less than about 60° C., less than about 50° C., less than about 45° C., less than about 40° C., less than about 35° C., less than about 30° C., less than about 25° C., less than about 20° C., or less than about 15° C. For example, the temperature of the cooled purge gas products in lines 120, 131, 138, and 146 can range from about 10° C. to about 45° C., about 15° C. to about 40° C., or about 15° C. to about 35° C.

Additionally, when a portion of the purge gas product is condensed between two compressors, the interstage pressure will drop as the purge gas product condenses, which results in a lower pressure ratio for the previous compression stage and a higher compression ratio for the subsequent compression stage. As such, temperature of the downstream compression stage can increase due to the condensing of the compressed purge gas product. Accordingly, the heat exchangers 118, 130, and/or 137 can be adapted to sufficiently cool the compressed purge gas introduced thereto so as to maintain the temperature of the compressed purge gas recovered from each compressor 128, 135, 142 at a desired temperature.

The condensed fluid recovered via lines 123, 140, and 152 can be recycled to the separator 132 and recovered as condensed fluid via line 133 therefrom. The condensed fluid via line 133 can be introduced to one or more pumps 156 to produce a pressurized condensed fluid via line 157. In another example, the condensed fluid via lines 123, 140, and/or 152 can be directly combined with the condensed fluid in line 133. In another example, the condensed fluid via lines 123, 140, and/or 152 can be introduced to separate pumps (not shown) to produce separate pressurized condensed fluids that can then be combined with the pressurized condensed fluid in line 157.

The condensed fluids via line 133, 148, and 152 can include one or more of the heavier hydrocarbons contained in the purge gas product in line 116. For example, when the purge gas product in line 116 contains ethylene and one or more comonomers such as butene, hexene, and/or octene, the major component(s) of the condensed fluids in lines 133, 148, and/ or 152 can include the one or more comonomers. As used herein, the term "major component" refers to a composition containing two or more components with the major component present in the greatest amount." For example, the major component of a two component composition would be present in an amount greater than 50%. In another example, the major component of a three component composition could be present in an amount as low as about 34%, with the amount of the other two components each less than 34%, e.g., about 33% or so. When the purge gas product in line 116 contains ethylene and one or more inert hydrocarbons, e.g., solvents, diluents, or induced condensing agents (ICAs), such as propane, butane, pentane, hexane, and/or octane, the major component(s) of the condensed fluids in lines 133, 148, and/or 152 can be the inert hydrocarbons. In another example, when the purge gas product in line 116 contains ethylene, one or more comonomers, and one or more inert hydrocarbons, the major component(s) of the condensed fluids in lines 133, 148, and/or 152 can be the comonomer(s) and the inert hydrocarbons.

Depending, at least in part, on the particular composition of the purge gas product in line 116, the composition of the condensed fluids in lines 133, 148, and/or 152 can widely vary. When the purge gas product contains inert hydrocarbons, e.g., iso-pentane, the concentration of the inert hydrocarbons in lines 133, 148, and/or 152 can range from a low of about 20 wt %, about 25 wt %, or about 30 wt % to a high of about 60 wt %, about 70 wt %, about 80 wt %, about 90 wt %, or about 95 wt %. When the purge gas product contains comonomers, the concentration of comonomers, e.g., butene, hexene, and/or octene, can range from a low of about 10 wt %, about 20 wt %, or about 30 wt % to a high of about 40 wt %, about 50 wt %, about 60 wt %, about 70 wt %, about 80 wt %, about 90 wt %, or about 95 wt %.

All or a portion of the pressurized condensed fluid in line 157 can be recycled via line 158 to the polymerization reactor 103. In another example, all or a portion of the pressurized condensed fluid in line 157 can be removed via line 159 from the polymerization system 100. For example, all or a portion of the pressurized condensed fluid via line 159 can be vented, flared, combusted to generate heat, or otherwise disposed. In another example, a first portion of the pressurized condensed fluid in line 157 can be recycled via line 158 to the polymerization reactor 103 and a second portion of the pressurized condensed fluid in line 157 can be removed via line 159 from the polymerization system 100. As shown, the condensed fluid recovered via line 148 from the separator 147 can be introduced via line 189 to the pressurized condensed fluid in line 158 and recycled to the polymerization reactor and/or introduced via line 188 to the pressurized condensed fluid in line 159 and removed from the polymerization system 100. Removing at least a portion of the pressurized condensed fluid via line 159 from the polymerization system 100 can reduce the buildup or accumulation of undesirable compounds such as inerts. The primary inert compounds that can be removed via line 159 can include, but are not limited to, hexane, butane, octane, 2-hexene, 3-hexene, and the like.

The amount of the pressurized condensed fluid via line 159 removed from the polymerization system 100 can range anywhere from about 1% to about 30% of the pressurized condensed fluid in line 157, which can also include any condensed fluid introduced via line 188 from the separator 147. For example, the amount of the pressurized condensed fluid in line 157 and the condensed fluid in line 148 removed via line 159 from the polymerization system 100 can range from a low of about 0.5%, about 1%, or about 2% to a high of about 5%, about 10%, about 20%, or about 25%. At times 100% of the pressurized condensed fluid in line 157 and the condensed fluid in line 148 can be recycled via line 158 to the polymerization reactor 103. In another example, all or a portion of the condensed fluid via lines 123, 133, 140, 148, and/or 152 can also be introduced to one or more of the compressors 128, 135, and/or 142. Introducing at least a portion of the condensed fluid via lines 123, 133, 140, 148, and/or 152 to one or more of the compressors 128, 134, and/or 142 can cause the condensed fluid to evaporate thereby lowering the temperature therein, thus lowering the temperature of the compressed product purge gas recovered therefrom.

Referring again to the compressed purge gas product in line 143, at least a portion of the compressed purge gas product in line 143 can be recycled via line 144 to the purge gas product in line 116 before the first compressor 128. The compressed purge gas product via line 144 can be recycled continuously or periodically depending on the flow rate of the purge gas product in line 116. For example, a portion of the compressed purge gas product via line 144 can be periodically recycled to the purge gas product in line 116 such that a minimum flow rate of fluid to the compression system 125 is maintained during the typically periodic or cyclic polymer product recovery process.

The compressed purge gas product via line 149 can be introduced to one or more refrigeration systems 160 to produce a plurality of products. The refrigeration system 160 may be an "auto-refrigeration system" that utilizes monomer as the refrigerant in a mixed composition cycle. For example, the refrigeration system 160 can produce a first product or "first recycle product" via line 174, a second product or "second recycle product" via line 178, and a third product or "third recycle product" via line 185. As discussed and described in more detail below, the first, second, and third products via lines 174, 178, and 185 can be portions or fractions of the compressed purge gas product in line 149. The first, second, and third products via lines 174, 178, and 185 can be produced by cooling, separating, and expanding the compressed purge gas product introduced via line 149 to the refrigeration system 160. As such, the refrigerant used within the refrigeration system 160 can be the compressed purge gas product or at least one or more components contained in the compressed purge gas product. For example, methane, ethylene, ethane, propylene, propane, butene, butane, nitrogen, or any combination thereof, can be contained in the compressed purge gas and any one or more of these components can be used, alone or in any combination, as the refrigerant within the refrigeration system 160. In another example, ethylene, ethane, and nitrogen in the compressed purge gas product can make up a majority of the refrigerant used within the refrigeration unit 160.

The compressed purge gas product via line 149 can be introduced to a multi-stage cooler 161. The multi-stage cooler 161 can expand three or more portions of the compressed purge gas product, as described in more detail below, to produce a cooled purge gas product via line 162. Although not shown, the multi-stage cooler 161 can be replaced with a plurality of separate heat exchangers or a combination of separate and combined heat exchangers.

The cooled compressed purge gas product in line 162 can be at a temperature of about −60° C. or less, about −65° C. or less, about −70° C. or less, about −75° C. or less, about −80° C. or less, about −85° C. or less, about −90° C. or less, or about −95° C. or less. For example, the temperature of the cooled compressed purge gas product in line 162 can range from about −72° C. to about −92° C., about −74° C. to about −88° C., or about −76° C. to about −86° C.

The cooled compressed purge gas product via line 162 can be introduced to one or more separators 163 to produce a gas product via line 164 and a condensed product via line 165. The gas product via line 164 can be introduced to one or more heat exchangers 166 to produce a further cooled gas product via line 167. The cooled gas product in line 167 can be at a temperature of about −70° C. or less, about −75° C. or less, about −80° C. or less, about −85° C. or less, about −90° C. or less, or about −95° C. or less. The temperature of the gas product in line 167 can be reduced by about 5° C., about 10° C., about 15° C., about 20° C., about 25° C., or about 30° C. as compared to the temperature of the gas product in line 164.

The cooled gas product via line 167 can be introduced to one or more separators 168 to produce a condensed product via line 169 and a gas product via line 170. The gas product via line 170 can be introduced to a first pressure reducing device 171 to produce an expanded gas product via line 172. The pressure of the expanded gas product in line 172 can be about 600 kPa or less, about 550 kPa or less, about 500 kPa or less, about 450 kPa or less, about 400 kPa or less, or about 380 kPa or less. For example, the pressure of the expanded gas product in line 172 can range from a low of about 101 kPa, about 150 kPa, or about 200 kPa to a high of about 375 kPa, about 400 kPa, or about 450 kPa. The temperature of the expanded gas product in line 172 can be less than about −100° C., less than about −105° C., less than about −110° C., less than about −120° C., less than about −125° C., or less than about −130° C. For example, the temperature of the expanded gas product in line 172 can be from about −105° C. to about −120° C., from about −110° C. to about −130° C., or from about −110° C. to about −140° C.

The expanded gas product via line 172 can be introduced to the heat exchanger 166 where heat can be indirectly transferred from the gas product introduced via line 164 to the expanded gas product. A first warmed first product via line 173 can be recovered from the heat exchanger 166 and introduced to the multi-stage heat exchanger 161 where heat can be transferred from the compressed purge gas product introduced via line 149 to the first warmed first product. As such, a first cooled compressed purge gas product can be produced by transferring heat from the compressed purge gas product introduced via line 149 to the multi-stage heat exchanger 161 and a second warmed first product via line 174 can be recovered from the multi-stage heat exchanger 161. Depending, at least in part, on the temperature of the compressed purge gas product in line 149, the temperature of the second warmed first product via line 174 can be about −20° C., about −10° C., about 0° C., about 20° C., about 30° C., or about 40° C. For example, the temperature of the first product via line 174 can range from about 0° C. to about 40° C., about 10° C. to about 40° C., 20° C. to about 40° C. or about 25° C. to about 35° C.

The refrigeration system or auto-refrigeration system 160 can produce the first product via line 174 having a low concentration of heavy hydrocarbons, e.g., $C_4$, $C_5$, $C_6$, and $C_7$ and heavier hydrocarbons. For a polymerization system 100 producing polyethylene, the first product in line 174 can include as a major component the purge gas (e.g., nitrogen) and as minor components hydrogen and/or light hydrocarbons (e.g., hydrogen, methane, ethylene, and ethane). For example, when the desired major component of the purge gas is nitrogen, the first product in line 174 can include about 70 wt % or more, about 75 wt % or more, about 80 wt % or more, about 85 wt % or more, about 90 wt % or more, or about 95 wt % or more nitrogen. The combined concentration of other effective purge gas components such as hydrogen, methane, ethylene, and ethane, can range from about 5 wt % to about 30 wt %. In another example, hydrogen, methane, ethane, and/or ethylene could be the major component of the purge gas. The first product in line 174 can have a concentration of $C_4$ hydrocarbons of less than about 500 parts per million by volume (ppmv), less than about 400 ppmv, less than about 300 ppmv, less than about 200 ppmv, less than about 100 ppmv, less than about 75 ppmv, or less than about 50 ppmv. The first product in line 174 can have a concentration of $C_5$ hydrocarbons of less than about 250 ppmv, less than about 200 ppmv, less than about 150 ppmv, less than about 100 ppmv, less than about 50 ppmv, less than about 40 ppmv, less than about 30 ppmv, or less than about 20 ppmv. The first product in line 174 can have a concentration of $C_6$ hydrocarbons of less than about 75 ppmv, less than about 50 ppmv, less than about 30 ppmv, less than about 15 ppmv, less than about 10 ppmv, or less than about 5 ppmv. The first product in line 174 can have a concentration of $C_7$ and heavier hydrocarbons of less than about 250 ppmv, less than about 200 ppmv, less than about 150 ppmv, less than about 100 ppmv, less than about 50 ppmv, less than about 40 ppmv, less than about 30 ppmv, or less than about 20 ppmv.

Since the first product in line 174 includes a relatively high concentration of light components, such as nitrogen and/or ethylene, and a low concentration of heavier components, the first product recovered via line 174 from the multi-stage heat exchanger 161 can be recycled to the purge bin 115 via line 112 as the purge gas. As such, the use of make-up or supplemental purge gas, such as nitrogen, can be reduced or eliminated and the purge gas via line 112 used to purge the polymer product of volatiles can be provided from the first product in line 174. A portion of the first product in line 174 can be removed via line 175 from the polymerization system 100 periodically or continuously. For example, the first product via line 175 can be vented, flared, combusted to generate heat, or otherwise removed from the polymerization system 100. A first portion of first product in line 174 can be recycled via line 112 to the purge bin 115 to provide at least a portion of the purge gas and a second portion of the first product in line 174 can be removed via line 175 from the polymerization system 100.

The amount of the first product in line 174 that can be vented, flared, or otherwise removed from the polymerization system 100 can range from about 1% to about 30% of the first product in line 174. For example, the amount of the first product in line 174 that can be removed via line 175 from the polymerization system 100 can range from a low of about 0.5%, about 1%, or about 2% to a high of about 5%, about 10%, about 20%, or about 25%. At times 100% of the first product via line 175 can be recycled via line 112 to the purge bin 115. Although not shown, at least a portion of the first product in line 174 can be recycled to compressor 128 via line 120. In another example not shown, the first product in line 175 can be compressed and introduced to the product discharge system 105 via line 107 to provide at least a portion of the product discharge assist gas.

Removing at least a portion of the first product via line 175 from the polymerization system 100 can primarily reduce the buildup of the purge gas, e.g., nitrogen, within the compression and refrigeration systems 125, 160. Other components that can be vented along with the nitrogen can primarily include lighter hydrocarbons such as methane, ethane, ethylene, propane, and/or propylene.

Referring again to the condensed product in line 165, a first portion of the condensed product in line 165 can be introduced to a second pressure reducing device 176 to produce an expanded or cooled product (second product) via line 177. The temperature of the second product in line 177 can be less than about −60° C., less than about −70° C., less than about −80° C., less than about −90° C., less than about −95° C., or less than about −100° C. For example, the temperature of the second product in line 177 can be from about −60° C. to about −110° C., from about −65° C. to about −90° C., or from about −70° C. to about −85° C.

When the polymer product comprises polyethylenes, the refrigeration system 160 can produce the second product via line 177 having a relatively high concentration of ethylene and ethane. For example, the combined concentration of ethylene and ethane in the second product in line 177 can be about 30 wt % or more, about 35 wt % or more about 40 wt % or more, about 45 wt % or more, about 50 wt % or more, about 55 wt % or more, about 60 wt % or more, about 65 wt % or more, or about 70 wt % or more. The concentration of ethylene in the second product in line 177 can range from a low of about 20 wt %, about 25 wt %, or about 30 wt % to a high of about 40 wt %, about 45 wt %, about 50 wt %, or about 55 wt %. When butene is used as a comonomer in producing the polyethylene products, the second product in line 177 can also have a relatively high concentration of butene and/or butane. For example, the second product in line 177 can have a combined concentration of butene and butane ranging from a low of about 10 wt %, about 15 wt %, or about 20 wt % to a high of about 30 wt %, about 35 wt %, or about 40 wt %. The concentration of butene in the second product in line 177 can range from a low of about 20 wt %, about 23 wt %, or about 25 wt % to a high of about 28 wt %, about 31 wt %, or about 35 wt %. When hexene is used as a comonomer in producing the polyethylene products, the second product in line 177 can have a hexene concentration ranging from a low of about 2 wt %, about 4 wt %, or about 6 wt % to a high of about 10 wt %, about 12 wt %, or about 14 wt %.

The second product via line 177 can be introduced to the multi-stage heat exchanger 161 where heat can be transferred from the compressed purge gas product introduced via line 149 to the second product. As such, the compressed purge gas product can be further cooled within the multi-stage heat exchanger 161 and a warmed second product via line 178 can be recovered therefrom. Depending, at least in part, on the temperature of the compressed second product in line 149, the temperature of the second product via line 178 can be about −20° C., about −10° C., about 0° C., about 20° C., about 30° C., or about 40° C. For example, the temperature of the second product via line 174 can range from about 0° C. to about 40° C., about 10° C. to about 40° C., 20° C. to about 40° C. or about 25° C. to about 35° C.

When the operating pressure of the reactor 103 is less than the pressure of the condensed product in line 165, it can be advantageous to maintain the pressure of the second product recovered via line 178 above the reactor pressure to allow some or all of the second product to be recycled to the reactor 103 via line 178 without requiring additional compression. The pressure of the second product in line 178 can range from a low of about 2,000 kPa, about 2,100 kPa, or about 2,300 kPa to a high of about 2,400 kPa, about 2,700 kPa, about 3,000 kPa, about 3,500 kPa, about 4,100 kPa, or about 4,900 kPa. Although not shown, one or more pumps can be used to increase the pressure of the condensed product in line 165 in order to increase the pressure of the second product recovered via line 178. For example, if the pressure within the reactor 103 is close to or greater than the pressure of the compressed purge gas product in line 149, the pressure of the condensed product in line 165 can be increased using one or more pumps in order to produce a second product via line 178 that can be directly recycled to the reactor 103. Although not shown, all or a portion of the second product via line 178 can be introduced to separation unit adapted to recover or separate an ethylene product therefrom.

A second portion of the condensed product in line 165 can be introduced via line 179 to a third pressure reducing device 180 to produce an expanded product via line 181. The pressure of the expanded product in line 181 can be about 600 kPa or less, about 550 kPa or less, about 500 kPa or less, about 450 kPa or less, about 400 kPa or less, or about 380 kPa or less. For example, the pressure of the expanded product in line 181 can range from a low of about 101 kPa, about 150 kPa, or about 200 kPa to a high of about 375 kPa, about 400 kPa, or about 450 kPa. The temperature of the expanded product in line 181 can be less than about −60° C., less than about −70° C., less than about −80° C., less than about −90° C., less than about −95° C., or less than about −100° C. For example, the temperature of the expanded product in line 181 can range from about −60° C. to about −110° C., or from about −65° C. to about −90° C., or from about −70° C. to about −85° C.

Referring again to the condensed product in line 169, the condensed product via line 169 can be introduced to a fourth pressure reducing device 182 to produce an expanded product via line 183. The pressure of the expanded product in line 183 can be about 600 kPa or less, about 550 kPa or less, about 500 kPa or less, about 450 kPa or less, about 400 kPa or less, or about 380 kPa or less. For example, the pressure of the expanded product in line 183 can range from a low of about 101 kPa, about 150 kPa, or about 200 kPa to a high of about 375 kPa, about 400 kPa, or about 450 kPa. The temperature of the expanded product in line 183 can be less than about −60° C., less than about −70° C., less than about −80° C., less than about −90° C., less than about −95° C., or less than about −100° C. For example, the temperature of the expanded product in line 183 can be from about −60° C. to about −110° C., from about −65° C. to about −90° C., or from about −70° C. to about −85° C.

The expanded product in line 183 and the expanded product in line 181 can be combined with one another to produce an expanded or cooled product (third product) via line 184. The cooled third product via line 184 can be introduced to the multi-stage heat exchanger 161 where heat can be transferred from the compressed purge gas product introduced via line 149 to the cooled third product. As such, the compressed purge gas product can be further cooled within the multi-stage heat exchanger 161 and a warmed third product via line 185 that includes the expanded products in lines 181 and 183 can be recovered from the multi-stage heat exchanger 161. Depending, at least in part, on the temperature of the compressed purge gas product in line 149, the temperature of the third product via line 185 can be about −20° C., about −10° C., about 0° C., about 20° C., about 30° C., or about 40° C. For example, the temperature of the third product via line 185 can range from about 0° C. to about 40° C., about 10° C. to about 40° C., 20° C. to about 40° C. or about 25° C. to about 35° C.

When the polymerization system 100 produces polyethylene products, the refrigeration system 160 can produce a third product via line 185 having a relatively high concentration of ethylene. At least a portion of the third product in line 185 can be recycled via line 186 to the purge gas product in line 116 or 120. When the polymerization system 100 produces polyethylene polymers, the third product in line 185 can have an ethylene concentration of about 20 wt % or more, about 25 wt % or more, about 30 wt % or more about 35 wt %, or more, about 40 wt % or more, about 45 wt % or more, about 50 wt % or more, about 55 wt % or more, or about 60 wt % or more. The third product in line 185 can have an ethane concentration ranging from a low of about 10 wt %, about 15 wt % or about 20 wt % to a high of about 25 wt %, about 30 wt %, about 35 wt %, or about 40 wt %. When butene is used as a comonomer in the production of polyethylenes, the third product in line 185 can have a butene concentration ranging from a low of about 5 wt %, about 10 wt %, or about 15 wt % to a high of about 20 wt %, about 25 wt %, or about 30 wt %. The concentration of other $C_4$ hydrocarbons can range from a low of about 1 wt %, about 2 wt %, or about 3 wt % to a high of about 4 wt %, about 5 wt %, or about 6 wt %.

At least a portion of the third product in line 185 can be removed via line 187 from the polymerization system 100. For example, at least a portion of the third product via line 187 can be vented, flared, combusted to generate heat, or otherwise removed from the polymerization system 100. In at least one example, a first portion of the third product via line 186 can be recycled to the purge gas product in line 116 or 120 and a second portion of the third product via line 187 can be removed from the polymerization system 100. Removing at least a portion of the third product via line 187 from the polymerization system 100 can reduce the concentration of undesired components thereby reducing or preventing the buildup of undesired components in the polymerization system 100. The undesired components that can be removed from the polymerization system 100 by removing at least a portion of the third product via line 187 therefrom can include, but are not limited to, inert compounds such as methane, ethane, propane, butane, and combinations thereof.

The amount of the third product removed via line 187 from the polymerization system 100 can range anywhere from 1% to about 50% of the third product in line 185. For example, the amount of the third product removed via line 187 from the polymerization system 100 can range from a low of about 1%, about 3%, or about 5% to a high of about 10%, about 15%, about 20%, about 25%, or about 30%. At times 100% of the third product in line 185 can be recycled via line 186 to the purge gas product in line 116. Although not shown, in another example all of the third product in line 185 can be recycled via line 186 to the purge gas product in line 116 or 120 and a portion of the second product in line 178 can be vented, flared, combusted to generate heat, or otherwise removed from the polymerization system 100 to reduce the buildup of undesired components in the polymerization system 100. In another example, a portion of the third product via line 186 and a portion of the second product in line 178 can be vented from the polymerization system 100.

The heat exchangers 118, 130, 137, 145, 161, and 166 can be or include any system, device, or combination of systems and/or devices suitable for indirectly transferring heat from one fluid to another fluid. For example, the heat exchangers can be or include one or more shell-and-tube, plate and frame, plate and fin, spiral wound, coil wound, U-tube, and/or bayonet style heat exchangers. In one or more embodiments, the one or more heat exchangers can also include surface enhanced tubes (e.g., fins, static mixers, rifling, heat conductive packing, turbulence causing projections, or any combination thereof), and the like. Although not shown, one or more of the heat exchanger 118, 130, 137, 145, 161, and 166 can include a plurality of heat exchangers. If a plurality of heat exchangers are used for any one or more of the heat exchangers 118, 130, 137, 145, 161, and 166 the heat exchangers can be of the same type or different type.

The separators 121, 132, 139, 147, 151, 163, and 168 can be or include any system, device, or combination of systems and/or devices suitable for separating gas from liquids. For example, the separators can be or include one or more flash tanks, distillation columns, fractionation columns, divided wall columns, or any combination thereof. The separators can contain one or more internal structures including, but not limited to, trays, random packing elements such as rings or saddles, structured packing, or any combination thereof. The separators can be or include an open column without internals. The separators can be a partially empty column containing one or more internal structures.

The compressors 128, 135, 142 can include any type of compressor. Illustrative compressors can include, but are not limited to, axial compressors, centrifugal compressors, rotary positive displacement compressors, diagonal or mixed-flow compressors, reciprocating compressors, dry screw compressors, oil flooded screw compressors, scroll compressors, and the like. The compressors 128, 135, 142 can be separate compressors or a single compressor having three or more compression stages. The compressors 128, 135, 142 can be powered by common or single motor, separate motors, or a combination thereof. The compressors 128, 135, 142 can be the same type of compressor or different. For example, the compressors 128, 135, 142 can all be reciprocating compressors. In another example, the first compressor 128 can be a dry screw compressor and the second and third compressors 135, 142 can be reciprocating compressors.

The pressure reducing devices 171, 176, 180 and 182 can be or include any system, device, or combination of systems and/or devices suitable for adiabatically or substantially adiabatically reducing the pressure of a compressed fluid. Illustrative pressure reducing devices can include, but are not limited to, valves, nozzles, orifices, porous plugs, and the like.

FIG. 2 depicts a schematic of an illustrative compression system 200 for compressing the purge gas product in line 116. The compression system 200 can be similar to the compression system 125 discussed and described above with reference to FIG. 1. The compression system 200 can further include a compressed purge gas product recycle line 205 in lieu of or in addition to the recycle line 144 (see FIG. 1).

The compression system 200 depicted in FIG. 2 is configured to increase the initial compressor volumes, i.e. increase the pressure ratio of the purge gas product compressed in an upstream compression stage relative to a later compression stage, thereby reducing the temperature of the later compressed purge gas product. In other words, the compression system 200 can provide a maximum pressure ratio the purge gas product is subjected to during compression in each stage by recycling a portion of the compressed purge gas product in line 205 to the compressed purge gas in line 129 and the compressed purge gas in line 136. As such, the pressure ratio of the compressed purge gas product recovered from each compressor 128, 135, 142 can be prevented from exceeding a predetermined pressure ratio for a particular compression stage, thereby fixing or substantially fixing the maximum discharge temperature of the compressed purge gas recovered from the compressors 128, 135, 142.

A first portion of the compressed purge gas product in line 205 can be recycled via line 215 to the compressed purge gas product in line 129 recovered from the first compressor 128. A second portion of the compressed purge gas product in line 205 can be recycled via line 210 to the compressed purge gas product in line 136 recovered from the second compressor 135. Although not shown, a third portion of the compressed purge gas product via line 144 (see FIG. 1) can be recycled to the purge gas product in line 116.

The amount of the compressed purge gas product in line 143 that can be recycled via lines 210, 215, and/or 144 can widely vary depending on the particular flow rate of the purge gas product introduced via line 116 to the compression system 200. The amount of compressed purge gas product recycled via lines 210, 215, and/or 144 can be adjusted to maintain a desired pressure ratio the purge gas product is subjected to within each compressor 128, 135, 142 such that the temperature of the compressed purge gas recovered from each compressor is maintained below the predetermined maximum temperature.

FIG. 3 depicts a schematic of an illustrative compression system 300 for compressing the purge gas product in line 116. The compression system 300 can be similar to the compression system 125 discussed and described above with reference to FIG. 1. The compression system 300 can further include compressed purge gas product recycle lines 305, 310, and 315 in lieu of or in addition to the recycle line 144 depicted in FIG. 1.

As shown, a portion of the compressed purge gas product in lines 129, 136, and 143 recovered from the first, second, and third compressors 128, 135, and 142, respectively, can be recycled to the purge gas product upstream of the respective compressor via lines 305, 310, and 315, respectively. As discussed above, the purge gas product can be maintained at or below a predetermined maximum temperature during compression thereof, and recycling a portion of the compressed purge gas product after each compression stage can provide control in adjusting the temperature of the compressed purge gas product after each compression stage 128, 135, 142.

As shown in FIG. 3, a portion of the compressed purge gas recovered from each compressor 128, 135, 142 can be recycled to the input of each compressor to provide a desired pressure ratio for each compressor. The desired pressure ratio for each compressor 128, 135, 142 can be determined, at least in part, based on the desired discharge temperature from each compressor for a particular purge gas product composition. Additionally, rather than recycling a portion of the compressed purge gas product via line 144 to the purge gas product in line 116 (as shown in FIG. 1) or recycling a portion of the purge gas product in line 143 via lines 210 and 215 to the compressed purge gas product in lines 129 and 136 (as shown in FIG. 2) a portion of the compressed purge gas product recovered via lines 129, 136, and 143 from each compressor 128, 135, and 142, respectively, can be recycled to the preceding purge gas product prior to introduction to the compressor. For example, a portion of the compressed purge gas product in line 129 can be recycled via line 305 to the purge gas product in line 116. A portion of the compressed purge gas product in line 136 can be recycled via line 310 to the compressed purge gas product in line 129. A portion of the compressed purge gas product in line 143 can be recycled via line 315 to the compressed purge gas product in line 136. Recycling a portion of the compressed purge gas product in lines 129, 136, and 143 via lines 305, 310, and 315, respectively, to the purge gas product in lines 116, 129, and 136, respectively, can result in a reduced or lower flow rate through the later compression stages because the recycle flows are not compounded from stage to stage. Additionally, recycling the compressed purge gas products via lines 305, 310, and 315 can reduce the overall power consumption because less purge gas product is compressed through the compression stages.

Figure 4:
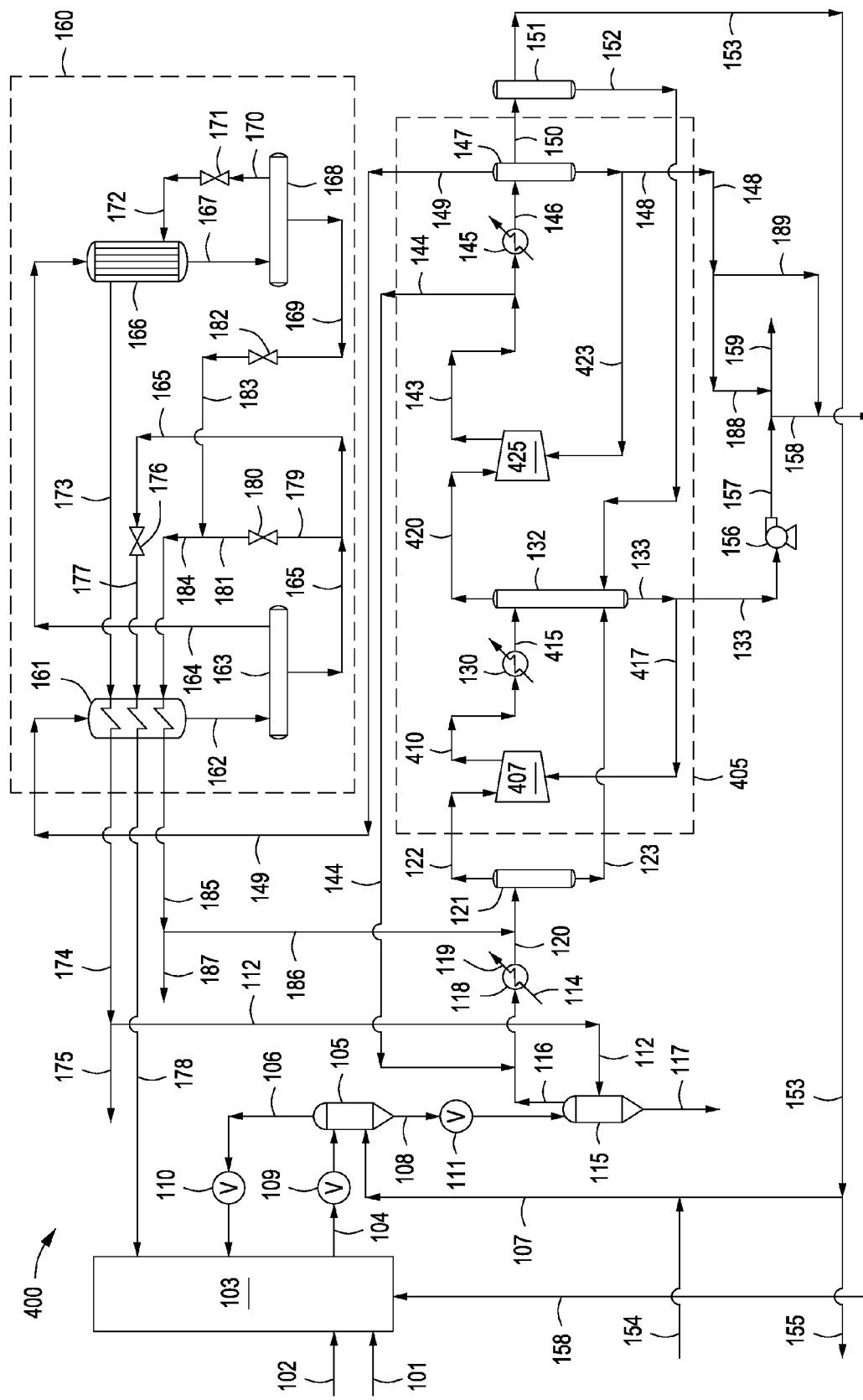
FIG. 4 depicts a schematic of an illustrative polymerization system for making one or more polymer products and recovering volatiles therefrom.

FIG. 4 depicts a schematic of an illustrative polymerization system 400 for making one or more polymer products and recovering volatiles therefrom. The polymerization system 400 can include the polymerization reactor 103; product discharge system 105; purge bin 115; heat exchangers 118, 130, and 145; separators 121, 132, 147 and 151; and refrigeration system 160, as discussed and described above with reference to FIG. 1. Rather than having three compressors 128, 135, and 142, however, the polymerization system 400 can include a compression system 405 having two compressors 407, 425.

The purge gas product via line 116, if desired, can be introduced to the heat exchanger 118 and the separator 121 to separate at least a portion of any condensed fluid via line 123 and provide the purge gas product via line 122, as discussed and described above with reference to FIG. 1.

The purge gas product via line 122 can be introduced to the compression system 405 to produce a compressed purge gas product via line 149 and a recovered, condensed product via lines 133 and/or 148. The compressed purge gas product in line 149 can be as discussed and described above with reference to FIG. 1. For example, the compressed purge gas product in line 149 can be at a pressure ranging from a low of about 2,500 kPa, about 2,700 kPa, about 3,100 kPa, about 3,500 kPa, about 4,000 kPa, or about 4,100 kPa to a high of about 5,000 kPa, about 6,000 kPa, about 7,000 kPa, about 8,000 kPa, about 9,000 kPa, or about 10,000 kPa. Depending, at least in part, on the particular composition of the purge gas product, e.g., the presence of catalytic components and/or the concentration of catalytic component(s) in the purge gas product, the temperature of the purge gas product can be maintained below about 250° C., below about 225° C., below about 200° C., below about 175° C., below about 150° C., below about 140° C., below about 130° C., below about 120° C., below about 110° C., or below about 100° C. during compression thereof.

The compressors 407 and 425 can compress the purge gas product at any desired pressure ratio. For example, the compressors 407 and 425 can compress the purge gas product at a pressure ratio ranging from a low of about 1:2, about 1:3, or about 1:4 to a high of about 1:5, about 1:6, about 1:7, about 1:8, about 1:9, or about 1:10. In another example, the compressors 407 and 425 can compress the purge gas product at a pressure ratio of about 1:3 to about 1:6, about 1:4 to about 1:9, about 1:5 to about 1:9, about 1:5 to about 1:8, about 1:6 to about 1:8, or about 1:4 to about 1:8. The particular pressure ratio within each compressor 407 and 425 can be based, at least in part, on the desired pressure of the compressed purge gas product produced via line 149, the particular components contained in the purge gas product in line 116, the type of compressor, the desired predetermined maximum temperature of the compressed purge gas after any particular compressor, or any combination thereof.

The pressure ratio at which the purge gas product is compressed within each compressor 407, 425 can be the same or different. The compressor 407 can compress the purge gas product at a pressure ratio equal to or greater than the compressor 425. For example, the compressor 407 can compress the purge gas product introduced via line 122 thereto at a pressure ratio of about 1:6 or more, about 1:6.5 or more, about 1:7 or more, about 1:7.5 or more, about 1:8 or more, or about 1:8.5 or more and the compressor 425 can compress the purge gas product at a pressure ratio equal to or less than the first compressor 407. The compressor 407 can compress the purge gas product at a pressure ratio equal to or less than the compressor 425. For example, the first compressor can compress the purge gas introduce via line 122 thereto at a pressure ratio of about 1:3 or less, about 1:4 or less, about 1:5 or less, about 1:6 or less, about 1:7 or less, or about 1:8 or less and the second compressor 425 can compress the purge gas product at a pressure ratio equal to or greater than the first compressor 407. The compressor 407 can compress the purge gas product at about the same pressure ratio as the compressor 425. For example, the compressors 407 and 425 can each compress the purge gas product introduced thereto at a pressure ratio of about 1:5, about 1:5.5, about 1:6, about 1:6.5, about 1:7, about 1:8, about 1:8.5, or about 1:9.

The compressed purge gas product recovered via lines 410 and 143 can have the same or different predetermined maximum temperature. The predetermined maximum temperature of the compressed purge gas product in line 410 can be equal to or greater than the predetermined maximum temperature of the purge gas product in line 143. For example, the predetermined maximum temperature of the compressed purge gas in line 410 can range from about 125° C. to about 250° C. and the predetermined maximum temperature of the compressed purge gas inline 143 can range from about 105° C. to about 200° C. The particular predetermined maximum temperature for any particular compressed purge gas via lines 410 and 143 can widely vary and can depend, at least in part, on the particular composition of the purge gas in line 116.

The compression system 405 can also include one or more heat exchangers and/or one or more separators that can cool and separate at least a portion of any condensed fluid from the compressed purge gas after one or both of the compression stages 407, 425. As shown, the compression system 405 includes the heat exchangers 130 and 145 that can be adapted to cool the compressed purge gas after each compression stage 407 and 425 and separators 132, and 147 that can separate at least a portion of any condensed fluid, if present, from the cooled compressed purge gas product recovered via lines 133 and 148 from the heat exchangers 130 and 145, respectively, as discussed and described above with reference to FIG. 1. For example, the compressed purge gas product recovered via line 415 from the first compressor 405 can be cooled within the heat exchanger 130 to produce a cooled first compressed purge gas product via line 415. The cooled first compressed purge gas product via line 415 can be introduced to the separator 132 to recover at least a portion of any condensed fluid via line 133 and a purge gas product via line 420. The purge gas product via line 420 can be compressed within the second compressor 425 and the compressed purge gas product via line 143 can be recovered therefrom. The purge gas product via line 143 can be introduced to heat exchanger 145 to produce a cooled purge gas product via line 146. The cooled purge gas product via line 146 can be introduced to the separator 147 to recover at least a portion of any condensed fluid via line 148 and the compressed purge gas product via line 149. Optionally, a portion of the purge gas product via line 150 can be recovered from the separator 147 and introduced to another separator 151 as discussed and described above with reference to FIG. 1 to produce the condensed fluid via line 152 and/or the purge gas product via line 153. The condensed fluid recovered via lines 123 and/or 152 can be recycled to the separator 132 and recovered therefrom via line 133.

The heat exchangers 118 and 130 can reduce the temperature of the purge gas product prior to introduction to the first and second compressors 407 and 425, respectively, a sufficient amount such that the temperature increase associated with the compression of the purge gas product within each compressor 407 and 425, and the temperature of the compressed purge gas recovered therefrom can be controlled. For example, the heat exchangers 118 and 130 can reduce the temperature of the purge gas product introduced via lines 116 and 410, respectively, such that the temperature of the purge gas product after each subsequent compression stage is maintained below about 250° C., about 225° C., about 200° C., about 175° C., about 150° C., about 140° C., about 130° C., about 120° C., about 115° C., about 110° C., about 105° C., or about 100° C.

The temperature of the cooled purge gas products recovered via lines 120, 415, and 146 from heat exchangers 118, 130, and 145, respectively, can be less than about 60° C., less than about 50° C., less than about 45° C., less than about 40° C., less than about 35° C., less than about 30° C., less than about 25° C., less than about 20° C., or less than about 15° C. For example, the temperature of the cooled purge gas products in lines 120, 415, and 146 can range from about 10° C. to about 45° C., about 15° C. to about 40° C., or about 15° C. to about 35° C. If a refrigeration system is used to cool the purge gas products in lines 116, 410, and/or 143 the temperature of the purge gas products recovered via lines 120, 415, and/or 146 can be about 15° C. or less, about 5° C. or less, about 0° C. or less, about −10° C. or less, or about −15° C. or less.

As shown, a portion of the condensed fluid in lines 133 and/or 148 can be recycled downstream to the compressors 407 and 425, respectively. For example, a portion of any condensed fluid in line 133 can be recycled via line 417 to the first compressor 407. Introducing a portion of the condensed fluid via line 417 to the compressor 407 can cool the compressed purge gas product via line 410 recovered therefrom. For example, the condensed fluid can be introduced to the compressor 407 and can expand therein which can remove heat from the purge gas compressed within the compressor 407. Similarly, a portion of the condensed fluid in line 148 can be recycled via line 423 to the second compressor 425. Although not shown, the recycled condensed fluid via lines 417 and/or 423 can be introduced to the purge gas product in lines 122 and/or 420. For example, the condensed fluid can be introduced to the purge gas product in lines 122 and/or 420 as an atomized liquid.

The compressed purge gas product recovered via line 149 from the compression system 405 can be introduced to the refrigeration system 160 and processed to produce the first, second, and third products via lines 174, 178, and 185 as discussed and described above with reference to FIG. 1. The condensed fluid via line 133 can be introduced to the pump 156 to produce the pressured condensed fluid via line 157 which can be recycled to the polymerization reactor 103 via line 158 and/or removed from the polymerization system 400 via line 159. Additionally, the condensed fluid via line 148 recovered from the separator 147 can be introduced to the pressurized condensed fluid in line 158 and recycled to the polymerization reactor 103 and/or the pressurized condensed fluid in line 159 and removed from the polymerization system 400.

The compressors 407 and 425 can include any type of compressor. Illustrative compressors can include, but are not limited to, axial compressors, centrifugal compressors, rotary positive displacement compressors, diagonal or mixed-flow compressors, reciprocating compressors, dry screw compressors, oil flooded screw compressors, scroll compressors, and the like. The compressors 407 and 425 can be powered via a single motor (not shown) or separate motors (not shown). The compressors 407 and 425 can be separate compressors or a single compressor having two compression stages. The compressors 407, 425 can be the same type of compressor or different types of compressors. For example, the first compressor 407 and the second compressor 425 can both be dry screw compressors. In another example, the first compressor 407 can be a dry screw compressor and the second compressor 425 can be a reciprocating compressor.

Figure 5:
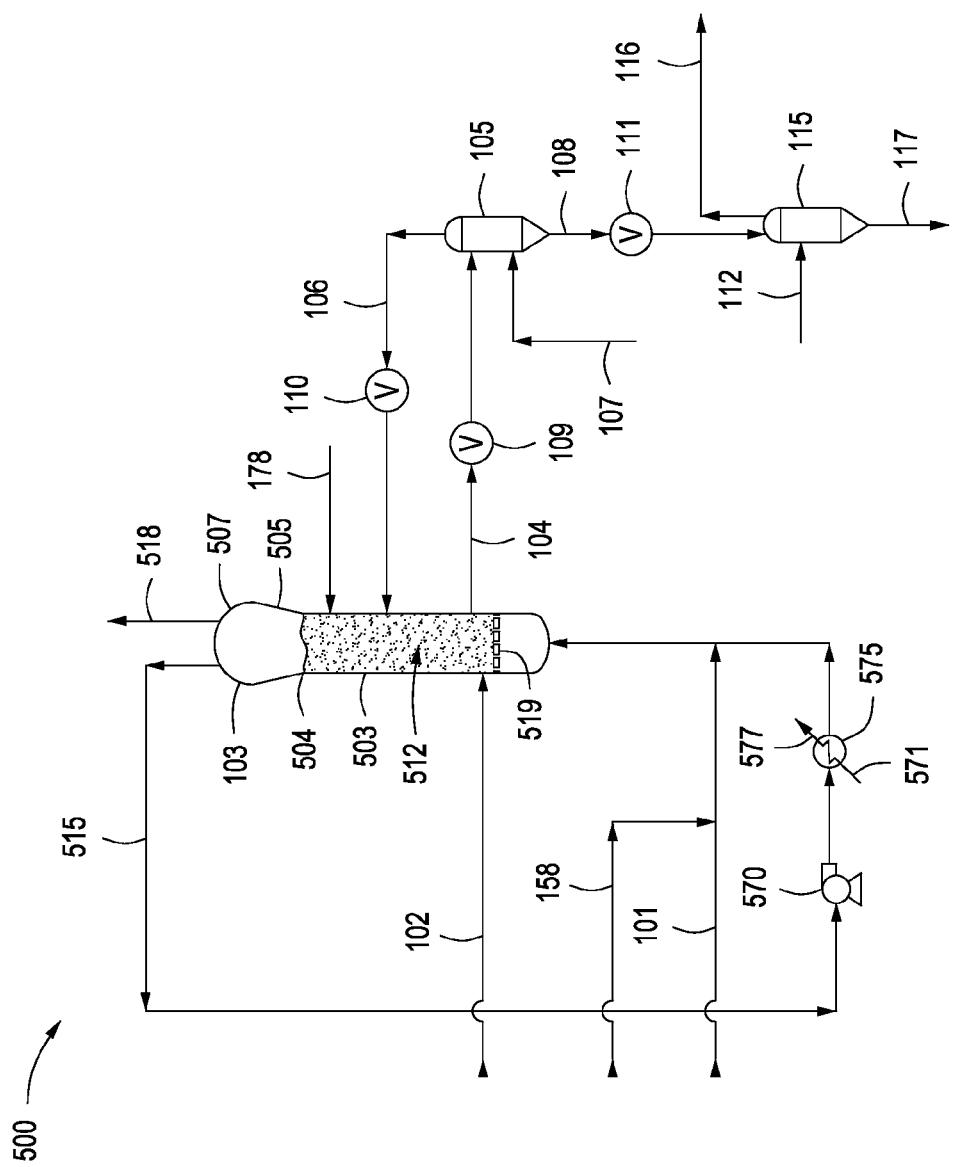
FIG. 5 depicts a schematic of an illustrative gas phase polymerization system.

FIG. 5 depicts a schematic of an illustrative gas phase polymerization system 500 for making polymers. The gas phase polymerization system 500 can be used to produce the polymer product via line 104 and the purge gas product via line 116 discussed and described above with reference to FIGS. 1-4. The polymerization system 500 can include one or more polymerization reactors 103, product discharge systems 105, purge bins 115, recycle compressors 570, and heat exchangers 575. The polymerization system 500 can include more than one reactor 103 arranged in series, parallel, or configured independent from the other reactors, each reactor having its own associated discharge tanks 105, recycle compressors 570, and heat exchangers 575, or alternatively, sharing any one or more of the associated discharge tanks 105, recycle compressors 570, and heat exchangers 575. For simplicity and ease of description, embodiments of the invention will be further described in the context of a single reactor train.

A plurality of reactors 103, however, can be used to produce a plurality of polymer products, from which at least a portion of the volatile components thereof can be removed via one or more product discharge systems 105 and one or more purge bins 115 to produce a plurality of purge gas products or a single purge gas product derived from a plurality of polymer products. For a plurality of polymerization systems 500, the multiple purge gas products recovered therefrom can be combined into a single purge gas product which can then be introduced to the compression system 125, 200, 300, or 405 and the refrigeration system 160 to separate the combined purge gas product into multiple components, as discussed and described above with reference to FIGS. 1-4. For example, two polymerization reactors 103 can be used to produce two different polyethylene products via lines 104 therefrom. The two different polyethylene products can be produced using different catalysts, ICAs, comonomers, and the like. The compression system 125, 200, 300, or 405 and/or the refrigeration system 160 can be configured to separate the different ICAs and/or the different comonomers from one another. At least a portion of the separated ICAs and different comonomers can be recycled to their respective polymerization reactors 103. As such, the compression system 125, 200, 300, or 405 and/or refrigeration system 160 can be used to separate and recycle various components of multiple purge gas products having different compositions to their respective polymerization reactors 103, thereby reducing the number of purge gas recovery systems required to separate purge gas products recovered from multiple polymerization systems.

When multiple purge gas products are recovered from multiple polymer products the composition of the purge gas products can be different. For example, an ethylene/butene copolymer product produced using iso-pentane as an ICA can produce a purge gas product containing ethylene, butene, and iso-pentane. An ethylene/hexene copolymer produced using hexane as an ICA can produce a purge gas product containing ethylene, hexene, and hexane. When those purge gas products having different compositions are combined and introduced to the compression system 125, 200, 300, or 405 and subsequently the refrigeration system 160, the various components can be separated or at least partially separated from one another with the compression 125, 200, 300, or 405 and/or refrigeration system 160. For example, the separators 121, 132, 139, 147, and 151 and the operating conditions thereof can be configured such that a particular component or components from the condensed purge gas product introduced thereto can be recovered therefrom. As such, the condensed products recovered via lines 123, 140, 152, and/or 148 can be recovered as independent products from the separators 121, 139, 147, and 151, respectively, and recycled to the appropriate location in their respective polymerization system. To improve the separation of the various components the separators 121, 132, 139, 147, and/or 151, as discussed above, can include baffles, packing material, trays, dividing walls, and the like in order to improve or enhance the separation of the different components in the condensed products introduced thereto. Similarly, the separators 163 and 168 can be adapted to separate multiple condensed and/or gaseous components introduced thereto.

The reactor 103 can include a cylindrical section 503, a transition section 505, and a velocity reduction zone or dome or "top head" 507. The cylindrical section 503 is disposed adjacent the transition section 505. The transition section 505 can expand from a first diameter that corresponds to the diameter of the cylindrical section 503 to a larger diameter adjacent the dome 507. The location or junction at which the cylindrical section 503 connects to the transition section 505 can be referred to as the "neck" or the "reactor neck" 504.

The cylindrical section 503 can include a reaction zone 512. The reaction zone can be a fluidized reaction bed or fluidized bed. In one or more embodiments, a distributor plate 519 can be disposed within the cylindrical section 503, generally at or toward the end of the cylindrical section that is opposite the end adjacent to the transition section 505. The reaction zone 512 can include a bed of growing polymer particles, formed polymer particles, and catalyst particles fluidized by the continuous flow of polymerizable and modifying gaseous components in the form of make-up feed and recycle fluid through the reaction zone 512.

One or more cycle fluid lines 515 and vent lines 518 can be in fluid communication with the dome 507 of the reactor 103. The polymer product can be recovered via line 104 from the reactor 103. A reactor feed via line 101 can be introduced to the polymerization system 500 at any location or combination of locations. For example, the reactor feed via line 101 can be introduced to the cylindrical section 503, the transition section 505, the velocity reduction zone 507, to any point within the cycle fluid line 515, or any combination thereof. Preferably, the reactor feed 101 is introduced to the cycle fluid in line 515 before or after the heat exchanger 575. The catalyst feed via line 102 can be introduced to the polymerization system 500 at any point. Preferably the catalyst feed via line 102 is introduced to a fluidized bed 512 within the cylindrical section 503.

In general, the height to diameter ratio of the cylindrical section 503 can vary in the range of from about 2:1 to about 5:1. The range, of course, can vary to larger or smaller ratios and depends, at least in part, upon the desired production capacity and/or reactor dimensions. The cross-sectional area of the dome 507 is typically within the range of from about 2 to about 3 multiplied by the cross-sectional area of the cylindrical section 503.

The velocity reduction zone or dome 507 has a larger inner diameter than the cylindrical section 503. As the name suggests, the velocity reduction zone 507 slows the velocity of the gas due to the increased cross-sectional area. This reduction in gas velocity allows particles entrained in the upward moving gas to fall back into the bed, allowing primarily only gas to exit overhead of the reactor 103 through the cycle fluid line 515. The cycle fluid recovered via line 515 can contain less than about 10 wt %, less than about 8 wt %, less than about 5 wt %, less than about 4 wt %, less than about 3 wt %, less than about 2 wt %, less than about 1 wt %, less than about 0.5 wt %, or less than about 0.2 wt % of the particles entrained in fluidized bed 512. In another example, the cycle fluid recovered via line 515 can have a particle concentration ranging from a low of about 0.001 wt % to about 5 wt %, from about 0.01 wt % to about 1 wt %, or from about 0.05 wt % to about 0.5 wt %, based on the total weight of the particle/cycle fluid mixture in line 515. For example, the particle concentration in the cycle fluid in line 515 can range from a low of about 0.001 wt %, about 0.01 wt %, about 0.05wt %, about 0.07 wt %, or about 0.1 wt % to a high of about 0.5 wt %, about 1.5 wt %, about 3 wt %, or about 4 wt %, based on the total weight of the cycle fluid and particles in line 515.

Suitable gas phase polymerization processes for producing the polymer product, e.g., a polyethylene polymer product, via line 104 are described in U.S. Pat. Nos. 3,709,853; 4,003, 712; 4,011,382; 4,302,566; 4,543,399; 4,588,790; 4,882,400; 5,028,670; 5,352,749; 5,405,922; 5,541,270; 5,627,242; 5,665,818; 5,677,375; 6,255,426; European Patent Nos. EP 0802202; EP 0794200; EP 0649992; EP 0634421. Other suitable polymerization processes that can be used to produce the polymer product can include, but are not limited to, solution, slurry, and high pressure polymerization processes. Examples of solution or slurry polymerization processes are described in U.S. Pat. Nos. 4,271,060; 4,613,484; 5,001,205; 5,236,998; and 5,589,555.

As noted above, the reactor feed in line 101 can include any polymerizable hydrocarbon of combination of hydrocarbons. For example, the reactor feed can be any olefin monomer including substituted and unsubstituted alkenes having two to 12 carbon atoms, such as ethylene, propylene, 1-butene, 1-pentene, 1-hexene, 1-heptene, 1-octene, 4-methylpent-1-ene, 1-decene, 1-dodecene, 1-hexadecene, and the like. The reactor feed in line 101 can also include non-hydrocarbon gas(es) such as nitrogen and/or hydrogen. The reactor feed via line 101 can enter the reactor at multiple and different locations. For example, reactor feed via line 101 can be introduced into the fluidized bed 512 in various ways including direct injection through a nozzle (not shown) into the fluidized bed. The polymer product in line 104 can thus be a homopolymer or a copolymer, including a terpolymer, having one or more other monomeric units.

As noted above, the reactor feed in line 101 can also include one or more modifying components such as one or more induced condensing agents or ICAs. Illustrative ICAs include, but are not limited to, propane, butane, isobutane, pentane, isopentane, hexane, isomers thereof, derivatives thereof, and combinations thereof. The ICAs can be introduced to provide a reactor feed 101 to the reactor 103 having an ICA concentration ranging from a low of about 1 mol %, about 5 mol %, or about 10 mol % to a high of about 25 mol %, about 35 mol %, or about 45 mol %. Typical concentrations of the ICAs can range from about 10 mol %, about 12 mol %, or about 14 mol % to a high of about 16 mol %, about 18 mol %, about 20 mol %, about 22 mol %, or about 24 mol %. The reactor feed 101 can include other non-reactive gases such as nitrogen and/or argon. Further details regarding ICAs are described in U.S. Pat. Nos. 5,352,749; 5,405,922; 5,436,304; and 7,122,607; and WO Publication No. 2005/113615 (A2). Condensing mode operation, such as disclosed in U.S. Pat. Nos. 4,543,399 and 4,588,790 can also be used to assist in heat removal from the polymerization reactor 103.

The catalyst feed in line 102 can include any catalyst or combination of catalysts. Illustrative catalysts can include, but are not limited to, Ziegler-Natta catalysts, chromium-based catalysts, metallocene catalysts and other single-site catalysts including Group 15-containing catalysts, bimetallic catalysts, and mixed catalysts. The catalyst can also include $AlCl_3$, cobalt, iron, palladium, chromium/chromium oxide or "Phillips" catalysts. Any catalyst can be used alone or in combination with any other catalyst.

Suitable metallocene catalyst compounds can include, but are not limited to, metallocenes described in U.S. Pat. Nos. 7,179,876; 7,169,864; 7,157,531; 7,129,302; 6,995,109; 6,958,306; 6,884,748; 6,689,847; 5,026,798; 5,703,187; 5,747,406; 6,069,213; 7,244,795; 7,579,415; U.S. Patent Application Publication No. 2007/0055028; and WO Publications WO 97/22635; WO 00/699/22; WO 01/30860; WO 01/30861; WO 02/46246; WO 02/50088; WO 04/022230; WO 04/026921; and WO 06/019494.

The "Group 15-containing catalyst" may include Group 3 to Group 12 metal complexes, wherein the metal is 2 to 8 coordinate, the coordinating moiety or moieties including at least two Group 15 atoms, and up to four Group 15 atoms. For example, the Group 15-containing catalyst component can be a complex of a Group 4 metal and from one to four ligands such that the Group 4 metal is at least 2 coordinate, the coordinating moiety or moieties including at least two nitrogens. Representative Group 15-containing compounds are disclosed in WO Publication No. WO 99/01460; European Publication Nos. EP0893454A1; EP 0894005A1; U.S. Pat. Nos. 5,318,935; 5,889,128; 6,333,389; and 6,271,325.

Illustrative Ziegler-Natta catalyst compounds are disclosed in European Patent Nos. EP 0103120; EP 1102503; EP 0231102; EP 0703246; U.S. Pat. Nos. RE 33,683; 4,115,639; 4,077,904; 4,302,565; 4,302,566; 4,482,687; 4,564,605; 4,721,763; 4,879,359; 4,960,741; 5,518,973; 5,525,678; 5,288,933; 5,290,745; 5,093,415; and 6,562,905; and U.S. Patent Application Publication No. 2008/0194780. Examples of such catalysts include those comprising Group 4, 5, or 6 transition metal oxides, alkoxides and halides, or oxides, alkoxides and halide compounds of titanium, zirconium or vanadium; optionally in combination with a magnesium compound, internal and/or external electron donors (alcohols, ethers, siloxanes, etc.), aluminum or boron alkyl and alkyl halides, and inorganic oxide supports.

Suitable chromium catalysts can include di-substituted chromates, such as $CrO_2(OR)_2$; where R is triphenylsilane or a tertiary polyalicyclic alkyl. The chromium catalyst system may further include $CrO_3$, chromocene, silyl chromate, chromyl chloride ($CrO_2Cl_2$), chromium-2-ethyl-hexanoate, or chromium acetylacetonate ($Cr(AcAc)_3$). Other non-limiting examples of chromium catalysts are described in U.S. Pat. No. 6,989,344 and WO2004/060923.

The mixed catalyst can be a bimetallic catalyst composition or a multi-catalyst composition. As used herein, the terms "bimetallic catalyst composition" and "bimetallic catalyst" include any composition, mixture, or system that includes two or more different catalyst components, each having a different metal group. The terms "multi-catalyst composition" and "multi-catalyst" include any composition, mixture, or system that includes two or more different catalyst components regardless of the metals. Therefore, the terms "bimetallic catalyst composition," "bimetallic catalyst," "multi-catalyst composition," and "multi-catalyst" will be collectively referred to herein as a "mixed catalyst" unless specifically noted otherwise. In one example, the mixed catalyst includes at least one metallocene catalyst component and at least one non-metallocene component.

In some embodiments, an activator may be used with the catalyst compound. As used herein, the term "activator" refers to any compound or combination of compounds, supported or unsupported, which can activate a catalyst compound or component, such as by creating a cationic species of the catalyst component. Illustrative activators include, but are not limited to, aluminoxane (e.g., methylaluminoxane "MAO"), modified aluminoxane (e.g., modified methylaluminoxane "MMAO" and/or tetraisobutyldialuminoxane "TIBAO"), and alkylaluminum compounds, ionizing activators (neutral or ionic) such as tri (n-butyl)ammonium tetrakis (pentafluorophenyl)boron may be also be used, and combinations thereof.

The catalyst compositions can include a support material or carrier. As used herein, the terms "support" and "carrier" are used interchangeably and are any support material, including a porous support material, for example, talc, inorganic oxides, and inorganic chlorides. The catalyst component(s) and/or activator(s) can be deposited on, contacted with, vaporized with, bonded to, or incorporated within, adsorbed or absorbed in, or on, one or more supports or carriers. Other support materials can include resinous support materials such as polystyrene, functionalized or crosslinked organic supports, such as polystyrene divinyl benzene polyolefins or polymeric compounds, zeolites, clays, or any other organic or inorganic support material, or mixtures thereof.

Suitable catalyst supports are described in U.S. Pat. Nos. 4,701,432; 4,808,561; 4,912,075; 4,925,821; 4,937,217; 5,008,228; 5,238,892; 5,240,894; 5,332,706; 5,346,925; 5,422,325; 5,466,649; 5,466,766; 5,468,702; 5,529,965; 5,554,704; 5,629,253; 5,639,835; 5,625,015; 5,643,847; 5,665,665; 5,698,487; 5,714,424; 5,723,400; 5,723,402; 5,731,261; 5,759,940; 5,767,032; 5,770,664; and 5,972,510; and WO Publication Nos. WO 95/32995; WO 95/14044; WO 96/06187; WO 97/02297; WO 99/47598; WO 99/48605; and WO 99/50311.

The cycle fluid via line 515 can be pressurized or compressed in the pump 570 and then introduced to the heat exchanger 575 where heat can be exchanged between the cycle fluid and a heat transfer medium. For example, during normal operating conditions a cool or cold heat transfer medium via line 571 can be introduced to the heat exchanger 575 where heat can be transferred from the cycle fluid in line 515 to produce a heated heat transfer medium via line 577 and a cooled cycle fluid via line 515. The terms "cool heat transfer medium" and "cold heat transfer medium" refer to a heat transfer medium having a temperature less than the fluidized bed 512 within the reactor 103. Illustrative heat transfer mediums can include, but are not limited to, water, air, glycols, or the like. It is also possible to locate the compressor 570 downstream from the heat exchanger 575 or at an intermediate point between several heat exchangers 575.

After cooling, all or a portion of the cycle fluid in line 515, the cycle fluid can be returned to the reactor 103. The cooled cycle fluid in line 515 can absorb the heat of reaction generated by the polymerization reaction. The heat exchanger 575 can be of any type of heat exchanger. Illustrative heat exchangers can include, but are not limited to, shell and tube, plate and frame, U-tube, and the like. For example, the heat exchanger 575 can be a shell and tube heat exchanger where the cycle fluid via line 515 can be introduced to the tube side and the heat transfer medium can be introduced to the shell side of the heat exchanger 575. If desired, to or more heat exchangers can be employed, in series, parallel, or a combination of series and parallel, to lower or increase the temperature of the cycle fluid in stages.

Preferably, the cycle gas via line 515 is returned to the reactor 103 and to the fluidized bed 512 through a fluid distributor plate ("plate") 519. The plate 519 can prevent polymer particles from settling out and agglomerating into a solid mass. The plate 519 can also prevent or reduce the accumulation of liquid at the bottom of the reactor 103. The plate 519 can also facilitate transitions between processes which contain liquid in the cycle stream 515 and those which do not and vice versa. Although not shown, the cycle gas via line 515 can be introduced into the reactor 103 through a deflector disposed or located intermediate an end of the reactor 103 and the distributor plate 519. Illustrative deflectors and distributor plates suitable for this purpose are described in U.S. Pat. Nos. 4,877,587; 4,933,149; and 6,627,713.

The catalyst feed via line 102 can be introduced to the fluidized bed 512 within the reactor 103 through one or more injection nozzles (not shown) in fluid communication with line 102. The catalyst feed is preferably introduced as preformed particles in one or more liquid carriers (i.e. a catalyst slurry). Suitable liquid carriers can include mineral oil and/or liquid or gaseous hydrocarbons including, but not limited to, butane, pentane, hexane, heptane, octane, isomers thereof, or mixtures thereof. A gas that is inert to the catalyst slurry such as, for example, nitrogen or argon can also be used to carry the catalyst slurry into the reactor 103. In one example, the catalyst can be a dry powder. In another example, the catalyst can be dissolved in a liquid carrier and introduced to the reactor 103 as a solution. The catalyst via line 102 can be introduced to the reactor 103 at a rate sufficient to maintain polymerization of the monomer(s) therein. The polymer product via line 104 can be discharged from the reactor 103 by operating flow control devices 109, 110, and 111. The polymer product via line 104 can be introduced to a plurality of purge bins or separation units, in series, parallel, or a combination of series and parallel, to further separate gases and/or liquids from the product. The particular timing sequence of the flow control devices 109, 110, 111, can be accomplished by use of conventional programmable controllers which are well known in the art. Other suitable product discharge systems are described in U.S. Pat. No. 6,548,610; U.S. Patent Application Publication No. 2010/014305; and PCT Publications WO2008/045173 and WO2008/045172.

The reactor 103 can be equipped with one or more vent lines 518 to allow venting the bed during start up, operation, and/or shut down. The reactor 103 can be free from the use of stirring and/or wall scraping. The cycle line 515 and the elements therein (compressor 570, heat exchanger 575) can be smooth surfaced and devoid of unnecessary obstructions so as not to impede the flow of cycle fluid or entrained particles.

The conditions for polymerization vary depending upon the monomers, catalysts, catalyst systems, and equipment availability. The specific conditions are known or readily derivable by those skilled in the art. For example, the temperatures can be within the range of from about −10° C. to about 140° C., often about 15° C. to about 120° C., and more often about 70° C. to about 110° C. Pressures can be within the range of from about 10 kPag to about 10,000 kPag, such as about 500 kPag to about 5,000 kPag, or about 1,000 kPag to about 2,200 kPag, for example. Additional details of polymerization can be found in U.S. Pat. No. 6,627,713.

In some embodiments, one or more continuity additives or static control agents can also be introduced to the reactor 103 to prevent agglomeration. As used herein, the term "continuity additive" refers to a compound or composition that when introduced into a reactor 103 can influence or drive the static charge (negatively, positively, or to zero) in the fluidized bed. Introducing continuity additive(s) can include the addition of negative charge generating chemicals to balance positive voltages or the addition of positive charge generating chemicals to neutralize negative voltage potentials. Antistatic substances can also be added, either continuously or intermittently to prevent or neutralize electrostatic charge generation. The continuity additive, if used, can be introduced with the reactor feed via line 101, the catalyst feed via line 102, a separate inlet (not shown), or any combination thereof. The particular continuity additive or combination of continuity additives can depend, at least in part, on the nature of the static charge, the particular polymer being produced within the polymerization reactor, the particular spray dried catalyst system or combination of catalyst systems being used, or a combination thereof. Suitable continuity additives are described in European Patent No. 0229368; U.S. Pat. Nos.

5,283,278; 4,803,251; 4,555,370; 4,994,534; and 5,200,477; and WO Publication No. WO2009/023111; and WO01/44322.

The use of the refrigeration/"auto-refrigeration" system 160 described herein can address several common problems with polyolefin purge gas systems, as it allows for the high nitrogen requirement for resin purging, reduces or eliminates ethylene losses in process vents, and reduces or eliminates reactive gases that cause fouling in the vent recovery system and fouling in general. The recovery system 160 described herein is also capable of processing a wide range of vent compositions.

The process described herein allows for condensation earlier in the compression train. This results in a reduced concentration of activators, such as triethyl aluminum alkyls (TEAL), in the gas due to absorption in the condensed liquids. The presence of activators/co-catalysts are believed to cause fouling in the vent recovery compressor over time, thus it is beneficial to have reduced concentrations in the compression train.

The system described herein may utilize atypical compression ratios, in that the compression ratio is stepped up going from the first stage to the third stage of the compressor. High compression ratios may lead to higher compressor discharge temperatures and higher pressures may lead to higher monomer partial pressure. Higher monomer partial pressure and higher temperatures may result in more reactive conditions. By using a lower compression ratio on the stages with the higher pressure (i.e., the first stage), the system described herein lowers the potential for fouling.

EXAMPLES

To provide a better understanding of the foregoing discussion, the following non-limiting examples are provided. Although the examples are directed to specific embodiments, they are not to be viewed as limiting the invention in any specific respect. All parts, proportions and percentages are by weight unless otherwise indicated.

Three simulated examples (Ex. 1-3) were prepared. The particular polymerization conditions used to produce the simulated results are shown in Table 1. The polymerization system for making polymer products and recovering volatiles therefrom was simulated using the polymerization system 100 discussed and described above with reference to FIG. 1, according to one or more embodiments. The computer simulation program ASPEN PLUS® from Aspen Technology, Inc. was used to generate the data for all three examples (Ex. 1-3). The simulations assume steady state modeling, rather than transient conditions such as equipment start-up. Compressor capacity is also calculated to match the minimum steady-state requirement for each simulation, as such no recycle of the compressed purge gas product to the input of the compressor(s) is included. The heat exchangers 118, 130, 137, and 145 are assumed to each cool the purge gas product stream to 35° C.

TABLE 1

Summary of Reaction Conditions Utilized in Examples 1-3

| | Example | | |
|---|---|---|---|
| | Ex. 1 | Ex. 2 | Ex. 3 |
| Melt Index ($I_2$) | 1 | 1 | 8.2 |
| Density (g/cm$^3$) | 0.918 | 0.918 | 0.963 |
| Fluidized Bed Temp. (° C.) | 91 | 87 | 102 |
| $C_2H_4$ Partial Pressure (psia) | 90 | 90 | 190 |
| $H_2/C_2$ | 0.99 | 0.131 | 0.344 |
| $C_4/C_2$ | 0.316 | 0 | 0 |
| $C_6/C_2$ | 0 | 0.127 | 0 |
| $C_x$ Incorporation (wt %) | 7.4 | 9.1 | — |
| TEAL, ppm (1) | 100 | 152 | 150 |
| Catalyst Type | Ziegler-Natta | Ziegler-Natta | Ziegler-Natta |
| Reactor Pressure (kPa) | 2,377 | 1,894 | 2,515 |
| Bulk Density (lbs/ft$^3$) | 24.5 | 22 | 27 |
| Fluidized Bulk Density (lbs/ft$^3$) | 14.5 | 15.4 | 19.4 |
| STY, lb/hr/ft$^3$ | 8 | 8 | 8 |

The first simulated example (Ex. 1) evaluates the separation of a purge gas product recovered from a linear low density ethylene/butene copolymer having a melt index ($I_2$) of 1.0 and a density of 0.918 g/cm$^3$. The second simulated example (Ex. 2) evaluates the separation of a purge gas product recovered from a linear low density ethylene/hexene copolymer having a melt index ($I_2$) of 1.0 and a density of 0.918 g/cm$^3$. The third simulated example (Ex. 3) evaluates the polymerization of a high density linear polyethylene homopolymer having a melt index ($I_2$) of about 8.2 and a density of about 0.963 g/cm$^3$. As shown in the tables below, the flow rate of the purge gas product via line 116 recovered from the purge bin 115 varies from about 5,558 kg/hr for Ex. 1 down to about 2,664 kg/hr for Ex. 3. The results of the three simulations for Examples 1-3 are shown in Tables 2A-C, 3A-C, and 4A-C, respectively. The stream numbers correspond to those discussed and described above with reference to FIG. 1.

TABLE 2A

Example 1

| | Stream | | | | | | | | | |
|---|---|---|---|---|---|---|---|---|---|---|
| | 116 | 122 | 129 | 133 | 134 | 136 | 141 | 143 | 188 | 189 |
| Hydrogen (wt %) | 0.11 | 0.1 | 0.1 | 0 | 0.1 | 0.1 | 0.13 | 0.13 | 0 | 0 |
| Methane (wt %) | 1.3 | 1.29 | 1.29 | 0.02 | 1.2 | 1.2 | 1.64 | 1.64 | 0.28 | 0.28 |
| Nitrogen (wt %) | 31.34 | 29.19 | 29.19 | 0.11 | 26.71 | 26.71 | 37.09 | 37.09 | 2.4 | 2.4 |
| Ethylene (wt %) | 9.36 | 11.23 | 11.23 | 0.59 | 10.64 | 10.64 | 14.13 | 14.13 | 6.32 | 6.32 |
| Ethane (wt %) | 4.35 | 5.35 | 5.35 | 0.43 | 5.14 | 5.14 | 6.68 | 6.68 | 3.95 | 3.95 |
| Butene (wt %) | 19.6 | 20.17 | 20.17 | 21.25 | 22.9 | 22.9 | 19.88 | 19.88 | 38.85 | 38.85 |
| C4 Inerts (wt %) | 2.66 | 2.74 | 2.74 | 2.9 | 3.11 | 3.11 | 2.7 | 2.7 | 5.2 | 5.2 |
| Hexene (wt %) | 0.00 | 0.00 | 0.00 | 0.00 | 0.00 | 0.00 | 0.00 | 0.00 | 0.00 | 0.00 |
| C6 Inerts (wt %) | 0.00 | 0.00 | 0.00 | 0.00 | 0.00 | 0.00 | 0.00 | 0.00 | 0.00 | 0.00 |

TABLE 2A-continued

Example 1

| | Stream | | | | | | | | | |
|---|---|---|---|---|---|---|---|---|---|---|
| | 116 | 122 | 129 | 133 | 134 | 136 | 141 | 143 | 188 | 189 |
| Iso-Pentane (wt %) | 27.44 | 25.96 | 25.96 | 70.58 | 25.72 | 25.72 | 13.84 | 13.84 | 35.43 | 35.43 |
| Normal Flow (kg/h) | 4237 | 4636 | 4636 | 990 | 5086 | 5086 | 3645 | 3645 | 55 | 1037 |
| Normal Flow (kg/s) | 1.1769 | 1.2876 | 1.2876 | 0.2751 | 1.4128 | 1.4128 | 1.0125 | 1.0125 | 0.0152 | 0.3035 |
| Temperature (° C.) | 91 | 34.5 | 110.3 | 19.4 | 19.4 | 87.4 | 35 | 124.1 | 35 | 35 |
| Pressure (kg/cm²a) | 1.1 | 1.09 | 3.94 | 3.92 | 3.92 | 12.65 | 12.55 | 42.18 | 42.07 | 42.07 |
| Density (kg/m³) | 1.39 | 1.62 | 4.74 | 619.11 | 6.48 | 17.37 | 17.69 | 46.81 | 563.09 | 563.09 |
| Specific Heat (kJ/kg-° C.) | 1.65 | 1.49 | 1.73 | 2.21 | 1.48 | 1.73 | 1.52 | 1.82 | 2.45 | 2.45 |
| Viscosity (cP) | 0.015 | 0.012 | 0.015 | | 0.011 | 0.014 | 0.013 | 0.018 | | |
| Thermal Conductivity (W/m-° C.) | 0.02 | 0.02 | 0.03 | | 0.02 | 0.03 | 0.02 | 0.03 | | |
| Compressibility | 1 | 0.99 | 0.99 | | 0.97 | 0.94 | 0.94 | 0.93 | | |
| Heat Capacity Ratio (Cp/Cv) | 1.15 | 1.17 | 1.15 | | 1.19 | 1.18 | 1.25 | 1.25 | | |
| Molecular Weight | 38.8 | 38.6 | 38.6 | 65.8 | 39.6 | 39.6 | 34.7 | 34.7 | 53.5 | 53.5 |
| Enthalpy (kJ/kg) | 3.04 | 2.85 | 0.98 | | 0.78 | 0.29 | 0.21 | 0.08 | | |
| Dewpoint (° C.) | −12.11 | −13.19 | 17.77 | 61.87 | 19.36 | 54.8 | 35 | 70.29 | 139.22 | 139.22 |
| Vapor Weight Fraction | 1 | 1 | 1 | | 1 | 1 | 1 | 1 | | |

TABLE 2B

Example 1

| | Stream | | | | | | | | | |
|---|---|---|---|---|---|---|---|---|---|---|
| | 150 | 149 | 157 | 158 | 159 | 162 | 165 | 177 | 178 | 164 |
| Hydrogen (wt %) | 0.19 | 0.19 | 0.00 | | 0.00 | 0.19 | 0.01 | 0.01 | 0.01 | 0.32 |
| Methane (wt %) | 2.22 | 2.22 | 0.02 | | 0.28 | 2.22 | 1.16 | 1.16 | 1.16 | 2.97 |
| Nitrogen (wt %) | 51.93 | 51.93 | 0.11 | | 2.40 | 51.93 | 5.67 | 5.67 | 5.67 | 84.26 |
| Ethylene (wt %) | 17.47 | 17.47 | 0.59 | | 6.32 | 17.47 | 28.87 | 28.87 | 28.87 | 9.5 |
| Ethane (wt %) | 7.85 | 7.85 | 0.43 | | 3.95 | 7.85 | 15.15 | 15.15 | 15.15 | 2.75 |
| Butene (wt %) | 11.76 | 11.76 | 21.25 | | 38.85 | 11.76 | 28.39 | 28.39 | 28.39 | 0.13 |
| C4 Inerts (wt %) | 1.63 | 1.63 | 2.90 | | 5.20 | 1.63 | 3.92 | 3.92 | 3.92 | 0.03 |
| Hexene (wt %) | 0.00 | 0.00 | 0.00 | | 0.00 | 0.00 | 0.00 | 0.00 | 0.00 | 0.00 |
| C6 Inerts (wt %) | 0.00 | 0.00 | 0.00 | | 0.00 | 0.00 | 0.00 | 0.00 | 0.00 | 0.00 |
| Iso-Pentane (wt %) | 4.59 | 4.59 | 70.58 | 1978 | 35.43 | 4.59 | 11.15 | 11.15 | 11.15 | 0.01 |
| Normal Flow (kg/h) | 1330 | 1223 | 941 | 1978 | 55 | 1223 | 503 | 95 | 95 | 720 |
| Normal Flow (kg/s) | 0.3694 | 0.3396 | 0.2614 | 0.5497 | 0.0152 | 0.3396 | 0.1397 | 0.0264 | 0.0264 | 0.1999 |
| Temperature (° C.) | 35 | 35 | 24.4 | | 35.0 | −69 | −69 | −69 | 30 | −69 |
| Pressure (kg/cm²a) | 42.07 | 42.07 | 28.12 | | 42.07 | 41.37 | 41.37 | 41.37 | 28.12 | 41.37 |
| Density (kg/m³) | 53.81 | 53.81 | 617.58 | | 563.09 | 114.52 | 614.87 | 614.87 | 82.82 | 73 |
| Specific Heat (kJ/kg-° C.) | 1.57 | 1.57 | 2.23 | | 2.45 | 1.68 | 2.01 | 2.01 | 2.31 | 1.44 |
| Viscosity (cP) | 0.016 | 0.016 | | | | 0.013 | | | 0.012 | 0.013 |
| Thermal Conductivity (W/m-° C.) | 0.03 | 0.03 | | | | 0.03 | | | 0.03 | 0.03 |
| Compressibility | 0.9 | 0.9 | | | | 0.87 | | | 0.8 | 0.87 |
| Heat Capacity Ratio (Cp/Cv) | 1.41 | 1.41 | | | | 1.71 | | | 1.45 | 1.71 |
| Molecular Weight | 30.2 | 30.2 | 65.8 | | 53.5 | 30.2 | 37.9 | 37.9 | 37.9 | 26.4 |
| Enthalpy (kJ/kg) | 0.02 | 0.02 | | | | 0.01 | | | 0 | 0.01 |
| Dewpoint (° C.) | 35 | 35 | 155.52 | | 139.22 | 34.65 | 81.57 | 81.57 | 69.43 | −69 |
| Vapor Weight Fraction | 1 | 1 | 0.00 | | 0.00 | 0.59 | | | 0.47 | 1 |

TABLE 2C

Example 1

| | Stream | | | | | | | | |
|---|---|---|---|---|---|---|---|---|---|
| | 167 | 169 | 170 | 173 | 112 | 175 | 184 | 186 | 187 |
| Hydrogen (wt %) | 0.32 | 0.01 | 0.33 | 0.33 | 0.33 | 0.33 | 0.01 | 0.01 | 0.01 |
| Methane (wt %) | 2.97 | 2.40 | 3.00 | 3.00 | 3.00 | 3.00 | 1.26 | 1.26 | 1.26 |
| Nitrogen (wt %) | 84.26 | 12.79 | 88.06 | 88.06 | 88.06 | 88.06 | 6.25 | 6.25 | 6.25 |
| Ethylene (wt %) | 9.50 | 56.65 | 7.00 | 7.00 | 7.00 | 7.00 | 31.14 | 31.14 | 31.14 |
| Ethane (wt %) | 2.75 | 24.20 | 1.61 | 1.61 | 1.61 | 1.61 | 15.89 | 15.89 | 15.89 |
| Butene (wt %) | 0.13 | 2.61 | 0.00 | 0.00 | 0.00 | 0.00 | 26.28 | 26.28 | 26.28 |
| C4 Inerts (wt %) | 0.03 | 0.51 | 0.00 | 0.00 | 0.00 | 0.00 | 3.65 | 3.65 | 3.65 |
| Hexene (wt %) | 0.00 | 0.00 | 0.00 | 0.00 | 0.00 | 0.00 | 0.00 | 0.00 | 0.00 |
| C6 Inerts (wt %) | 0.00 | 0.00 | 0.00 | 0.00 | 0.00 | 0.00 | 0.00 | 0.00 | 0.00 |
| Iso-Pentane (wt %) | 0.01 | 0.24 | 0.00 | 0.00 | 0.00 | 0.00 | 10.26 | 10.26 | 10.26 |

TABLE 2C-continued

Example 1

| | Stream | | | | | | | | |
|---|---|---|---|---|---|---|---|---|---|
| | 167 | 169 | 170 | 173 | 112 | 175 | 184 | 186 | 187 |
| Normal Flow (kg/h) | 720 | 36 | 683 | 683 | 575 | 108 | 444 | 399 | 45 |
| Normal Flow (kg/s) | 0.1999 | 0.0101 | 0.1898 | 0.1898 | 0.1598 | 0.03 | 0.1234 | 0.1108 | 0.0126 |
| Temperature (° C.) | −90.4 | −90.4 | −90.4 | −71 | 30 | 30 | −94.6 | 30 | 30 |
| Pressure (kg/cm$^2$a) | 41.37 | 41.37 | 41.37 | 3.87 | 3.52 | 3.52 | 1.55 | 1.2 | 1.2 |
| Density (kg/m$^3$) | 89.42 | 563.72 | 85.6 | 6.02 | 3.61 | 3.61 | 14.95 | 1.74 | 1.74 |
| Specific Heat (kJ/kg-° C.) | 1.58 | 2.25 | 1.55 | 1.14 | 1.17 | 1.17 | 1.7 | 1.59 | 1.59 |
| Viscosity (cP) | 0.013 | | 0.013 | 0.012 | 0.017 | 0.017 | 0.007 | 0.01 | 0.01 |
| Thermal Conductivity (W/m-° C.) | 0.02 | | 0.02 | 0.02 | 0.03 | 0.03 | 0.01 | 0.02 | 0.02 |
| Compressibility | 0.82 | | 0.82 | 0.99 | 1 | 1 | 0.98 | 0.99 | 0.99 |
| Heat Capacity Ratio (Cp/Cv) | 1.85 | | 1.85 | 1.42 | 1.38 | 1.38 | 1.4 | 1.17 | 1.17 |
| Molecular Weight | 26.4 | 28.5 | 26.3 | 26.3 | 26.3 | 26.3 | 36.9 | 36.9 | 36.9 |
| Enthalpy (kJ/kg) | 0.01 | | 0.01 | 0.11 | 0.16 | 0.03 | 0.03 | 0.23 | 0.03 |
| Dewpoint (° C.) | −69 | 3.57 | −90.44 | −116.96 | −117.98 | −117.98 | −16.16 | −21.64 | −21.64 |
| Vapor Weight Fraction | 0.95 | | 1 | 1 | 1 | 1 | 0.19 | 1 | 1 |

The simulated data shown in Tables 2A-C in which the polymerization of the ethylene/butene copolymer is produced, shows that the purge gas introduced via line 122 to the compression system 125 contains about 30 wt % nitrogen, 11 wt % ethylene (monomer), about 5 wt % ethane, about 20 wt % butene (comonomer), about 3 wt % C$_4$ inerts, and about 26 wt % iso-pentane (ICA) and has a normal flow rate of about 4,636 kg/h, which includes the third product recovered from the multi-stage cooler 161 and recycled via line 186 line to the purge gas in line 116.

The maximum temperature the purge gas product reaches during separation of the purge gas is 124.1° C. as the compressed purge gas product via line 143 exits the third compressor 142. The pressure ratio at which the first compressor 128 compresses the purge gas product is greater than the second and third compressors 135, 142. More particularly, the compressed purge gas product recovered via line 129 from the first compressor 128 is compressed at a pressure ratio of 1:3.61, the compressed purge gas product recovered via line 136 from the second compressor is compressed at a pressure ratio of 1:3.23, and the compressed purge gas product recovered via line 143 from the third compressor 142 is compressed at a pressure ratio of 1:3.36. Additionally, the heat exchangers 118, 130, and 137 cool the purge gas product and the compressed purge gas products introduced thereto via lines 116, 129, and 136 to a temperature of 34.5° C., 19.4° C., and 35° C., respectively further reducing the temperature increase caused by the compression.

The compressed purge gas recovered via line 149 from the compression system 125 is at a pressure of about 42.07 kg/cm$^2$a (about 4,130 kPa) and a temperature of about 35° C. The cooled purge gas recovered via line 162 from the multi-stage heat exchanger 161 is separated within the gas/liquid separator 163 to produce the gas product via line 164 and the condensed product via line 165 at a temperature of about −69° C. Expansion and/or further separation of the gas product via line 164 and the condensed product via line 165 yields three cooled products, namely the first product via line 173, the second product via line 177, and the third product via line 184 at temperatures of −71° C., −69° C., and −94.6° C., respectively.

Also shown in Tables 2A-C, the compression and auto-refrigeration systems 125, 160 provide sufficient separation of the various components of the purge gas product, i.e. the nitrogen (purge gas), ethylene (monomer), and isopentene/butene (ICA/comonomer) such that the separated components can be recycled within the polymerization system 100 at the appropriate locations rather than having to be vented, flared, combusted as fuel, or otherwise removed from the polymerization system. For example, the first product via line 174 is sufficiently high in light components, including in this case nitrogen at 88 wt % and sufficiently low in heavy components (e.g., butene at <0.005 wt % and iso-pentane at <0.005 wt %) that the first product can be used as the purge gas via line 112 for purging the polymer product. In another example, the second product via line 178 is sufficiently high in light hydrocarbons (ethylene at about 28.8 wt %, ethane at about 15.1 wt %, and butene 28.4 wt %) that the second product via line 178 can be recycled back to the polymerization reactor 103, thereby recycling monomer (ethylene) and comonomer (butene) thereto. Additionally, since the second product via line 178 is at a pressure of about 2,760 kPa, the second product via line 178 can be recycled directly to the polymerization reactor 103 that is operated at a pressure of about 2,377 kPa without additional compression. In another example, the third product in line 185 contains about 31.1 wt % ethylene, about 15.9 wt % ethane, and about 26.3 wt % butene. As such, at least a portion of the third product in line 185 can be recycle via line 186 to the purge gas product in line 116, which can increase the concentration of the lighter components, e.g., ethylene and ethane, in the compressed purge gas product in line 149 to maintain a desired level of refrigerant within the auto-refrigeration system 160.

TABLE 3A

Example 2

| | Stream | | | | | | | | | |
|---|---|---|---|---|---|---|---|---|---|---|
| | 116 | 122 | 129 | 133 | 134 | 136 | 141 | 143 | 188 | 189 |
| Hydrogen (wt %) | 0.27 | 0.25 | 0.25 | 0.00 | 0.34 | 0.34 | 0.40 | 0.40 | 0.01 | 0.01 |
| Methane (wt %) | 0.11 | 0.11 | 0.11 | 0.00 | 0.14 | 0.14 | 0.17 | 0.17 | 0.01 | 0.01 |
| Nitrogen (wt %) | 40.34 | 38.41 | 38.41 | 0.12 | 51.23 | 51.23 | 61.42 | 61.42 | 1.80 | 1.80 |
| Ethylene (wt %) | 8.41 | 10.56 | 10.56 | 0.40 | 14.11 | 14.11 | 16.67 | 16.67 | 4.34 | 4.34 |
| Ethane (wt %) | 5.67 | 7.45 | 7.45 | 0.42 | 9.95 | 9.95 | 11.67 | 11.67 | 4.32 | 4.32 |
| Butene (wt %) | 0.00 | 0.00 | 0.00 | 0.00 | 0.00 | 0.00 | 0.00 | 0.00 | 0.00 | 0.00 |
| C4 Inerts (wt %) | 0.00 | 0.00 | 0.00 | 0.00 | 0.00 | 0.00 | 0.00 | 0.00 | 0.00 | 0.00 |
| Hexene (wt %) | 19.31 | 18.54 | 18.54 | 41.45 | 11.21 | 11.21 | 4.77 | 4.77 | 42.21 | 42.21 |
| C6 Inerts (wt %) | 25.90 | 24.68 | 24.68 | 57.60 | 13.01 | 13.01 | 4.89 | 4.89 | 47.32 | 47.32 |
| Iso-Pentane (wt %) | 0.00 | 0.00 | 0.00 | 0.00 | 0.00 | 0.00 | 0.00 | 0.00 | 0.00 | 0.00 |
| Normal Flow (kg/h) | 5558 | 5929 | 5929 | 2226 | 4445 | 4445 | 3703 | 3703 | | 226 |
| Normal Flow (kg/s) | 1.5439 | 1.6469 | 1.6469 | 0.6183 | 1.2349 | 1.2349 | 1.0286 | 1.0286 | | 0.0626 |
| Temperature (° C.) | 87.0 | 34.6 | 114.1 | 34.8 | 34.8 | 127.5 | 35.0 | 151.6 | 35.0 | 35.0 |
| Pressure (kg/cm$^2$a) | 1.10 | 1.09 | 3.94 | 3.92 | 3.92 | 12.65 | 12.55 | 42.18 | 42.07 | 42.07 |
| Density (kg/m$^3$) | 1.40 | 1.60 | 4.60 | 654.14 | 4.87 | 12.08 | 14.03 | 33.83 | 633.60 | 633.60 |
| Specific Heat (kJ/kg-° C.) | 1.58 | 1.46 | 1.68 | 2.20 | 1.40 | 1.60 | 1.38 | 1.58 | 2.25 | 2.25 |
| Viscosity (cP) | 0.016 | 0.014 | 0.017 | | 0.015 | 0.019 | 0.016 | 0.021 | | |
| Thermal Conductivity (W/m-° C.) | 0.03 | 0.02 | 0.03 | | 0.03 | 0.03 | 0.03 | 0.04 | | |
| Compressibility | 1.00 | 0.99 | 0.99 | | 0.99 | 0.99 | 0.98 | 0.99 | | |
| Heat Capacity Ratio (Cp/Cv) | 1.16 | 1.18 | 1.16 | | 1.24 | 1.22 | 1.31 | 1.28 | | |
| Molecular Weight | 38.5 | 38.0 | 38.0 | 83.8 | 32.0 | 32.0 | 28.6 | 28.6 | 70.6 | 70.6 |
| Enthalpy (kJ/kg) | 3.98 | 3.72 | 1.29 | | 0.91 | 0.37 | 0.26 | 0.11 | | |
| Dewpoint (° C.) | 24.61 | 22.95 | 55.57 | 115.01 | 34.76 | 65.08 | 35.00 | 59.43 | 212.47 | 212.47 |
| Vapor Weight Fraction | 1.00 | 1.00 | 1.00 | 0.00 | 1.00 | 1.00 | 1.00 | 1.00 | 0.00 | 0.00 |

TABLE 3B

Example 2

| | Stream | | | | | | | | | |
|---|---|---|---|---|---|---|---|---|---|---|
| | 150 | 149 | 157 | 158 | 159 | 162 | 165 | 177 | 178 | 164 |
| Hydrogen (wt %) | 0.43 | 0.43 | 0.00 | | 0.00 | 0.43 | 0.01 | 0.01 | 0.01 | 0.58 |
| Methane (wt %) | 0.18 | 0.18 | 0.00 | | 0.00 | 0.18 | 0.11 | 0.11 | 0.11 | 0.21 |
| Nitrogen (wt %) | 65.29 | 65.29 | 0.12 | | 0.12 | 65.29 | 8.77 | 8.77 | 8.77 | 86.36 |
| Ethylene (wt %) | 17.47 | 17.47 | 0.40 | | 0.40 | 17.47 | 40.67 | 40.67 | 40.67 | 8.82 |
| Ethane (wt %) | 12.14 | 12.14 | 0.42 | | 0.42 | 12.14 | 33.91 | 33.91 | 33.91 | 4.02 |
| Butene (wt %) | 0.00 | 0.00 | 0.00 | | 0.00 | 0.00 | 0.00 | 0.00 | 0.00 | 0.00 |
| C4 Inerts (wt %) | 0.00 | 0.00 | 0.00 | | 0.00 | 0.00 | 0.00 | 0.00 | 0.00 | 0.00 |
| Hexene (wt %) | 2.35 | 2.35 | 41.45 | | 41.45 | 2.35 | 8.64 | 8.64 | 8.64 | 0.00 |
| C6 Inerts (wt %) | 2.14 | 2.14 | 57.60 | | 57.60 | 2.14 | 7.89 | 7.89 | 7.89 | 0.00 |
| Iso-Pentane (wt %) | 0.00 | 0.00 | 0.00 | | 0.00 | 0.00 | 0.00 | 0.00 | 0.00 | 0.00 |
| Normal Flow (kg/h) | 1349 | 1997 | 2115 | 2341 | 111 | 1997 | 542 | 204 | 204 | 1454 |
| Normal Flow (kg/s) | 0.3748 | 0.5547 | 0.5874 | 0.65 | 0.0309 | 0.5547 | 0.1507 | 0.0566 | 0.0566 | 0.4040 |
| Temperature (° C.) | 35.0 | 35.0 | 39.4 | 34.8 | −77.2 | −77.2 | −77.2 | 30.0 | −77.2 | |
| Pressure (kg/cm$^2$a) | 42.07 | 42.07 | 28.12 | 3.92 | 41.37 | 41.37 | 41.37 | 28.12 | 41.37 | |
| Density (kg/m$^3$) | 46.80 | 46.80 | 653.17 | 654.14 | 98.93 | 584.74 | 584.74 | 47.14 | 75.53 | |
| Specific Heat (kJ/kg-° C.) | 1.45 | 1.45 | 2.21 | 2.20 | 1.66 | 2.17 | 2.17 | 2.01 | 1.47 | |
| Viscosity (cP) | 0.017 | 0.017 | | | 0.013 | | | 0.012 | 0.013 | |
| Thermal Conductivity (W/m-° C.) | 0.03 | 0.03 | | | 0.03 | | | 0.03 | 0.03 | |
| Compressibility | 0.95 | 0.95 | | | 0.86 | | | 0.82 | 0.86 | |
| Heat Capacity Ratio (Cp/Cv) | 1.41 | 1.41 | | | 1.73 | | | 1.44 | 1.73 | |
| Molecular Weight | 27.5 | 27.5 | 83.8 | 83.8 | 27.5 | 32.3 | 32.3 | 32.3 | 26.1 | |
| Enthalpy (kJ/kg) | 0.03 | 0.04 | | | 0.02 | | | 0.00 | 0.02 | |
| Dewpoint (° C.) | 35.00 | 35.00 | 221.58 | 115.01 | 34.80 | 78.55 | 78.55 | 71.70 | −77.20 | |
| Vapor Weight Fraction | 1.00 | 1.00 | 0.00 | 0.00 | 0.73 | 0.00 | 0.00 | 0.82 | 1.00 | |

TABLE 3C

Example 2

| | Stream | | | | | | | | |
|---|---|---|---|---|---|---|---|---|---|
| | 167 (26) | 169 (27) | 170 (28) | 173 (30) | 112 (31) | 175 (32) | 184 (34) | 186 (36) | 187 (35) |
| Hydrogen (wt %) | 0.58 | 0.02 | 0.62 | 0.62 | 0.62 | 0.62 | 0.01 | 0.01 | 0.01 |
| Methane (wt %) | 0.21 | 0.17 | 0.21 | 0.21 | 0.21 | 0.21 | 0.12 | 0.12 | 0.12 |
| Nitrogen (wt %) | 86.36 | 12.59 | 90.51 | 90.51 | 90.51 | 90.51 | 9.48 | 9.48 | 9.48 |
| Ethylene (wt %) | 8.82 | 52.13 | 6.38 | 6.38 | 6.38 | 6.38 | 42.80 | 42.80 | 42.80 |
| Ethane (wt %) | 4.02 | 35.08 | 2.28 | 2.28 | 2.28 | 2.28 | 34.13 | 34.13 | 34.13 |
| Butene (wt %) | 0.00 | 0.00 | 0.00 | 0.00 | 0.00 | 0.00 | 0.00 | 0.00 | 0.00 |
| C4 Inerts (wt %) | 0.00 | 0.00 | 0.00 | 0.00 | 0.00 | 0.00 | 0.00 | 0.00 | 0.00 |
| Hexene (wt %) | 0.00 | 0.01 | 0.00 | 0.00 | 0.00 | 0.00 | 7.03 | 7.03 | 7.03 |
| C6 Inerts (wt %) | 0.00 | 0.01 | 0.00 | 0.00 | 0.00 | 0.00 | 6.42 | 6.42 | 6.42 |
| Iso-Pentane (wt %) | 0.00 | 0.00 | 0.00 | 0.00 | 0.00 | 0.00 | 0.00 | 0.00 | 0.00 |
| Normal Flow (kg/h) | 1454 | 77 | 1377 | 1377 | 1282 | 95 | 416 | 371 | 45 |
| Normal Flow (kg/s) | 0.4040 | 0.0215 | 0.3825 | 0.3825 | 0.3560 | 0.0265 | 0.1156 | 0.1030 | 0.0126 |
| Temperature (° C.) | −90.2 | −90.2 | −90.2 | −80.8 | 30.0 | 30.0 | −102.0 | 30.0 | 30.0 |
| Pressure (kg/cm$^2$a) | 41.37 | 41.37 | 41.37 | 3.87 | 3.52 | 3.52 | 1.55 | 1.20 | 1.20 |
| Density (kg/m$^3$) | 85.87 | 567.85 | 81.96 | 6.23 | 3.56 | 3.56 | 14.41 | 1.48 | 1.48 |
| Specific Heat (kJ/kg-° C.) | 1.54 | 2.25 | 1.51 | 1.15 | 1.18 | 1.18 | 1.81 | 1.60 | 1.60 |
| Viscosity (cP) | 0.013 | | 0.013 | 0.012 | 0.017 | 0.017 | 0.008 | 0.011 | 0.011 |
| Thermal Conductivity (W/m-° C.) | 0.03 | | 0.03 | 0.02 | 0.03 | 0.03 | 0.01 | 0.02 | 0.02 |
| Compressibility | 0.84 | | 0.84 | 0.99 | 1.00 | 1.00 | 0.98 | 0.99 | 0.99 |
| Heat Capacity Ratio (Cp/Cv) | 1.78 | | 1.78 | 1.42 | 1.38 | 1.38 | 1.41 | 1.20 | 1.20 |
| Molecular Weight | 26.1 | 28.6 | 26.0 | 26.0 | 26.0 | 26.0 | 31.5 | 31.5 | 31.5 |
| Enthalpy (kJ/kg) | 0.02 | | 0.02 | 0.22 | 0.36 | 0.03 | 0.03 | 0.25 | 0.03 |
| Dewpoint (° C.) | −77.20 | −2.10 | −90.16 | −119.08 | −120.24 | −120.24 | 1.39 | −3.44 | −3.44 |
| Vapor Weight Fraction | 0.95 | 0.00 | 1.00 | 1.00 | 1.00 | 1.00 | 0.21 | 1.00 | 1.00 |

The simulated data shown in Tables 3A-C in which the polymerization of the ethylene/hexene copolymer is produced, shows that the purge gas product introduced via line 122 to the compression system 125 contains about 38.4 wt % nitrogen, 10.6 wt % ethylene (monomer), about 5.7 wt % ethane, about 18.5 wt % hexene (comonomer), and about 24.7 wt % $C_6$ inerts and has a normal flow rate of about 5,929 kg/h, which includes the third product recovered from the multi-stage cooler 161 and recycled via line 186 line to the purge gas in line 116.

The maximum temperature the purge gas product reaches during separation of the purge gas is 151.6° C. as the compressed purge gas via line 143 exits the third compressor 142. The pressure ratio at which the first compressor 128 compresses the purge gas product is greater than the second and third compressors 135, 142. More specifically, the simulated example conditions utilized the same pressure ratios for the compressors 128, 135, 142 as in Ex. 1, which are 1:3.61, 1:3.23, and 1:3.36, respectively. Additionally, the heat exchangers 118, 130, and 137 cool the purge gas product and the compressed purge gas products introduced thereto via lines 116, 129, and 136 to a temperature of 34.6° C., 34.8° C., and 35.0° C., respectively further reducing the temperature increase caused by the compression.

The compressed purge gas recovered via line 149 from the compression system 125 is at a pressure of about 42.07 kg/cm$^2$a (about 4,130 kPa) and a temperature of about 35° C. The cooled purge gas recovered via line 162 from the multi-stage heat exchanger 161 is separated within the gas/liquid separator 163 to produce the gas product via line 164 and the condensed product via line 165 at a temperature of about −77.2° C. Expansion and/or further separation of the gas product via line 164 and the condensed product via line 165 yields three cooled products, namely the first product via line 173, the second product via line 177, and the third product via line 184 at temperatures of −116° C., −77.2° C., and −102.0° C., respectively.

Also shown in Tables 3A-C, the compression and auto-refrigeration systems 125, 160 provide sufficient separation of the various components of the purge gas product, i.e. the nitrogen (purge gas), ethylene (monomer), and isopentene/butene (ICA/comonomer) such that the separated components can be recycled within the polymerization system 100 at the appropriate locations rather than having to be vented, flared, combusted as fuel, or otherwise removed from the polymerization system. For example, the first product via line 174 is sufficiently high in light components, including in this case nitrogen at 90.5 wt % and sufficiently low in heavy components (e.g., butene at <0.005 wt % and iso-pentane at <0.005 wt %) that the first product can be used as the purge gas via line 112 for purging the polymer product. In another example, the second product via line 178 is sufficiently high in light hydrocarbons (ethylene at about 40.7 wt % and ethane at about 33.9 wt %) that the second product via line 178 can be recycled back to the polymerization reactor 103, thereby recycling monomer (ethylene) and comonomer (butene) thereto. Additionally, since the second product via line 178 is at a pressure of about 2,760 kPa, the second product via line 178 can be recycled directly to the polymerization reactor 103 that is operated at a pressure of about 1,894 kPa without additional compression. In another example, the third product in line 185 contains about 42.8 wt % ethylene and about 34.1 wt % ethane. As such, at least a portion of the third product in line 185 can be recycle via line 186 to the purge gas product in line 116, which can increase the concentration of the lighter components, e.g., ethylene and ethane, in the compressed purge gas product in line 149 to maintain a desired level of refrigerant within the auto-refrigeration system 160.

TABLE 4A

Example 3

| | \multicolumn{10}{c}{Stream} |
|---|---|---|---|---|---|---|---|---|---|---|
| | 116 | 122 | 129 | 133 | 134 | 136 | 141 | 143 | 188 | 189 |
| Hydrogen (wt %) | 1.02 | 0.89 | 0.89 | 0.00 | 0.80 | 0.80 | 0.93 | 0.93 | 0.02 | 0.02 |
| Methane (wt %) | 1.70 | 1.65 | 1.65 | 0.02 | 1.50 | 1.50 | 1.74 | 1.74 | 0.22 | 0.22 |
| Nitrogen (wt %) | 34.36 | 30.47 | 30.47 | 0.09 | 27.49 | 27.49 | 31.99 | 31.99 | 1.48 | 1.48 |
| Ethylene (wt %) | 22.66 | 26.77 | 26.77 | 1.08 | 24.48 | 24.48 | 28.06 | 28.06 | 9.68 | 9.68 |
| Ethane (wt %) | 6.67 | 8.01 | 8.01 | 0.49 | 7.36 | 7.36 | 8.38 | 8.38 | 3.85 | 3.85 |
| Butene (wt %) | 0.00 | 0.00 | 0.00 | 0.00 | 0.00 | 0.00 | 0.00 | 0.00 | 0.00 | 0.00 |
| C4 Inerts (wt %) | 0.00 | 0.00 | 0.00 | 0.00 | 0.00 | 0.00 | 0.00 | 0.00 | 0.00 | 0.00 |
| Hexene (wt %) | 0.99 | 0.87 | 0.87 | 9.43 | 1.03 | 1.03 | 0.45 | 0.45 | 1.69 | 1.69 |
| C6 Inerts (wt %) | 0.01 | 0.01 | 0.01 | 0.11 | 0.01 | 0.01 | 0.00 | 0.00 | 0.01 | 0.01 |
| Iso-Pentane (wt %) | 32.59 | 31.32 | 31.32 | 88.78 | 37.33 | 37.33 | 28.45 | 28.45 | 83.04 | 83.04 |
| Normal Flow (kg/h) | 2664 | 3092 | 3092 | 147 | 3432 | 3432 | 2945 | 2945 | 0 | 643 |
| Normal Flow (kg/s) | 0.7399 | 0.8590 | 0.8590 | 0.0409 | 0.9534 | 0.9534 | 0.8181 | 0.8181 | 0.0000 | 0.1786 |
| Temperature (° C.) | 108.0 | 34.3 | 125.6 | 15.6 | 15.6 | 93.1 | 35.0 | 128.8 | 35.0 | 35.0 |
| Pressure (kg/cm$^2$a) | 1.10 | 1.09 | 3.94 | 3.92 | 3.92 | 12.65 | 12.55 | 42.18 | 42.07 | 42.07 |
| Density (kg/m$^3$) | 1.03 | 1.27 | 3.55 | 635.38 | 5.25 | 13.48 | 14.80 | 38.31 | 576.52 | 576.52 |
| Specific Heat (kJ/kg-° C.) | 1.79 | 1.59 | 1.86 | 2.16 | 1.57 | 1.83 | 1.66 | 1.97 | 2.40 | 2.40 |
| Viscosity (cP) | 0.017 | 0.013 | 0.017 | | 0.012 | 0.016 | 0.014 | 0.018 | | |
| Thermal Conductivity (W/m-° C.) | 0.04 | 0.03 | 0.04 | | 0.02 | 0.03 | 0.03 | 0.04 | | |
| Compressibility | 1.00 | 1.00 | 0.99 | | 0.98 | 0.97 | 0.96 | 0.95 | | |
| Heat Capacity Ratio (Cp/Cv) | 1.19 | 1.21 | 1.18 | | 1.22 | 1.20 | 1.26 | 1.25 | | |
| Molecular Weight | 30.0 | 30.3 | 30.3 | 71.3 | 32.1 | 32.1 | 29.5 | 29.5 | 58.1 | 58.1 |
| Enthalpy (kJ/kg) | 2.60 | 2.43 | 0.87 | | 0.65 | 0.25 | 0.20 | 0.08 | | |
| Dewpoint (° C.) | −16.92 | −17.88 | 9.86 | 76.19 | 15.62 | 47.59 | 35.00 | 67.23 | 159.36 | 159.36 |
| Vapor Weight Fraction | 1.00 | 1.00 | 1.00 | 0.00 | 1.00 | 1.00 | 1.00 | 1.00 | 0.00 | 0.00 |

TABLE 4B

Example 3

| | \multicolumn{10}{c}{Stream} |
|---|---|---|---|---|---|---|---|---|---|---|
| | 150 | 149 | 157 | 158 | 159 | 162 | 165 | 177 | 178 | 164 |
| Hydrogen (wt %) | 1.19 | 1.19 | 0.00 | | 0.00 | 1.19 | 0.04 | 0.04 | 0.04 | 2.50 |
| Methane (wt %) | 2.16 | 2.16 | 0.02 | | 0.02 | 2.16 | 1.36 | 1.36 | 1.36 | 3.08 |
| Nitrogen (wt %) | 40.51 | 40.51 | 0.09 | | 0.09 | 40.51 | 6.11 | 6.11 | 6.11 | 79.97 |
| Ethylene (wt %) | 33.19 | 33.19 | 1.08 | | 1.08 | 33.19 | 51.40 | 51.40 | 51.40 | 12.30 |
| Ethane (wt %) | 9.65 | 9.65 | 0.49 | | 0.49 | 9.65 | 16.19 | 16.19 | 16.19 | 2.14 |
| Butene (wt %) | 0.00 | 0.00 | 0.00 | | 0.00 | 0.00 | 0.00 | 0.00 | 0.00 | 0.00 |
| C4 Inerts (wt %) | 0.00 | 0.00 | 0.00 | | 0.00 | 0.00 | 0.00 | 0.00 | 0.00 | 0.00 |
| Hexene (wt %) | 0.10 | 0.10 | 9.43 | | 9.43 | 0.10 | 0.18 | 0.18 | 0.18 | 0.00 |
| C6 Inerts (wt %) | 0.00 | 0.00 | 0.11 | | 0.11 | 0.00 | 0.00 | 0.00 | 0.00 | 0.00 |
| Iso-Pentane (wt %) | 13.21 | 13.21 | 88.78 | | 88.78 | 13.21 | 24.71 | 24.71 | 24.71 | 0.01 |
| Normal Flow (kg/h) | 1038 | 1243 | 147 | 783 | 0 | 1243 | 664 | 192 | 192 | 579 |
| Normal Flow (kg/s) | 0.2883 | 0.3452 | 0.0409 | 0.2174 | 0.0000 | 0.3452 | 0.1844 | 0.0533 | 0.0533 | 0.1608 |
| Temperature (° C.) | 35.0 | 35.0 | 20.6 | | 15.6 | −79.2 | −79.2 | −79.2 | 30.0 | −79.2 |
| Pressure (kg/cm$^2$a) | 42.07 | 42.07 | 3.92 | | 3.92 | 41.37 | 41.37 | 41.37 | 28.12 | 41.37 |
| Density (kg/m$^3$) | 45.62 | 45.62 | 635.38 | | 635.38 | 112.10 | 586.14 | 586.14 | 50.10 | 58.15 |
| Specific Heat (kJ/kg-° C.) | 1.77 | 1.77 | 2.16 | | 2.16 | 1.92 | 2.10 | 2.10 | 2.06 | 1.71 |
| Viscosity (cP) | 0.015 | 0.015 | | | | 0.012 | | | 0.012 | 0.012 |
| Thermal Conductivity (W/m-° C.) | 0.04 | 0.04 | | | | 0.04 | | | 0.03 | 0.04 |
| Compressibility | 0.92 | 0.92 | | | | 0.90 | | | 0.81 | 0.90 |
| Heat Capacity Ratio (Cp/Cv) | 1.40 | 1.40 | | | | 1.63 | | | 1.45 | 1.63 |
| Molecular Weight | 25.9 | 25.9 | 71.3 | | 71.3 | 25.9 | 32.9 | 32.9 | 32.9 | 20.8 |
| Enthalpy (kJ/kg) | 0.02 | 0.03 | | | | 0.01 | | | 0.00 | 0.01 |
| Dewpoint (° C.) | 35.00 | 35.00 | 76.19 | | 76.19 | 34.70 | 64.61 | 64.61 | 55.72 | −79.20 |
| Vapor Weight Fraction | 1.00 | 1.00 | 0.00 | | 0.00 | 0.47 | 0.00 | 0.00 | 0.79 | 1.00 |

TABLE 4C

Example 3

| | Stream | | | | | | | | |
|---|---|---|---|---|---|---|---|---|---|
| | 167 | 169 | 170 | 173 | 112 | 175 | 184 | 186 | 187 |
| Hydrogen (wt %) | 2.50 | 0.06 | 2.61 | 2.61 | 2.61 | 2.61 | 0.04 | 0.04 | 0.04 |
| Methane (wt %) | 3.08 | 2.00 | 3.13 | 3.13 | 3.13 | 3.13 | 1.39 | 1.39 | 1.39 |
| Nitrogen (wt %) | 79.97 | 9.37 | 83.13 | 83.13 | 83.13 | 83.13 | 6.27 | 6.27 | 6.27 |
| Ethylene (wt %) | 12.30 | 69.67 | 9.73 | 9.73 | 9.73 | 9.73 | 52.32 | 52.32 | 52.32 |
| Ethane (wt %) | 2.14 | 18.62 | 1.41 | 1.41 | 1.41 | 1.41 | 16.31 | 16.31 | 16.31 |
| Butene (wt %) | 0.00 | 0.00 | 0.00 | 0.00 | 0.00 | 0.00 | 0.00 | 0.00 | 0.00 |
| C4 Inerts (wt %) | 0.00 | 0.00 | 0.00 | 0.00 | 0.00 | 0.00 | 0.00 | 0.00 | 0.00 |
| Hexene (wt %) | 0.00 | 0.00 | 0.00 | 0.00 | 0.00 | 0.00 | 0.17 | 0.17 | 0.17 |
| C6 Inerts (wt %) | 0.00 | 0.00 | 0.00 | 0.00 | 0.00 | 0.00 | 0.00 | 0.00 | 0.00 |
| Iso-Pentane (wt %) | 0.01 | 0.29 | 0.00 | 0.00 | 0.00 | 0.00 | 23.49 | 23.49 | 23.49 |
| Normal Flow (kg/h) | 579 | 25 | 554 | 554 | 451 | 103 | 497 | 429 | 68 |
| Normal Flow (kg/s) | 0.1608 | 0.0069 | 0.1539 | 0.1539 | 0.1252 | 0.0287 | 0.1380 | 0.1191 | 0.0189 |
| Temperature (° C.) | −89.8 | −89.8 | −89.8 | −81.1 | 30.0 | 30.0 | −102.6 | 30.0 | 30.0 |
| Pressure (kg/cm$^2$a) | 41.37 | 41.37 | 41.37 | 3.87 | 3.52 | 3.52 | 1.55 | 1.20 | 1.20 |
| Density (kg/m$^3$) | 63.88 | 553.72 | 61.44 | 4.94 | 2.82 | 2.82 | 15.65 | 1.53 | 1.53 |
| Specific Heat (kJ/kg-° C.) | 1.77 | 2.27 | 1.75 | 1.44 | 1.49 | 1.49 | 1.75 | 1.61 | 1.61 |
| Viscosity (cP) | 0.012 | | 0.012 | 0.011 | 0.016 | 0.016 | 0.007 | 0.010 | 0.010 |
| Thermal Conductivity (W/m-° C.) | 0.04 | | 0.04 | 0.03 | 0.05 | 0.05 | 0.01 | 0.02 | 0.02 |
| Compressibility | 0.89 | | 0.89 | 0.99 | 1.00 | 1.00 | 0.98 | 0.99 | 0.99 |
| Heat Capacity Ratio (Cp/Cv) | 1.66 | | 1.66 | 1.42 | 1.38 | 1.38 | 1.42 | 1.20 | 1.20 |
| Molecular Weight | 20.8 | 27.8 | 20.6 | 20.6 | 20.6 | 20.6 | 32.6 | 32.6 | 32.6 |
| Enthalpy (kJ/kg) | 0.01 | | 0.01 | 0.11 | 0.16 | 0.04 | 0.03 | 0.28 | 0.04 |
| Dewpoint (° C.) | −79.20 | −4.92 | −89.80 | −120.40 | −121.54 | −121.54 | −16.65 | −21.70 | −21.70 |
| Vapor Weight Fraction | 0.96 | 0.00 | 1.00 | 1.00 | 1.00 | 1.00 | 0.18 | 1.00 | 1.00 |

The simulated data shown in Tables 4A-C in which the polymerization of the ethylene homopolymer is produced, shows that the purge gas introduced via line 122 to the compression system 125 contains about 30.5 wt % nitrogen, 26.8 wt % ethylene (monomer), about 8 wt % ethane, and about 31.3 wt % iso-pentane and has a normal flow rate of about 3,092 kg/h, which includes the third product recovered from the multi-stage cooler 161 and recycled via line 186 line to the purge gas in line 116.

The maximum temperature the purge gas product reaches during separation of the purge gas is 128.8° C. as the compressed purge gas product via line 143 exits the third compressor 142. The pressure ratio at which the first compressor 128 compresses the purge gas product is greater than the second and third compressors 135, 142. More specifically, the simulated example conditions utilized the same pressure ratios for the compressors 128, 135, 142 as in Ex. 1, which are 1:3.61, 1:3.23, and 1:3.36, respectively. Additionally, the heat exchangers 118, 130, and 137 cool the purge gas product and the compressed purge gas products introduced thereto via lines 116, 129, and 136 to a temperature of 34.3° C., 15.6° C., and 35.0° C., respectively further reducing the temperature increase caused by the compression.

The compressed purge gas recovered via line 149 from the compression system 125 is at a pressure of about 42.07 kg/cm$^2$a (about 4,130 kPa) and a temperature of about 35° C. The cooled purge gas recovered via line 162 from the multi-stage heat exchanger 161 is separated within the gas/liquid separator 163 to produce the gas product via line 164 and the condensed product via line 165 at a temperature of about −79.2° C. Expansion and/or further separation of the gas product via line 164 and the condensed product via line 165 yields three cooled products, namely the first product via line 173, the second product via line 177, and the third product via line 184 at temperatures of −108.7° C., −79.2° C., and −102.6° C., respectively.

Also shown in Tables 4A-C, the compression and auto-refrigeration systems 125, 160 provide sufficient separation of the various components of the purge gas product, i.e. the nitrogen (purge gas), ethylene (monomer), and isopentene/butene (ICA/comonomer) such that the separated components can be recycled within the polymerization system 100 at the appropriate locations rather than having to be vented, flared, combusted as fuel, or otherwise removed from the polymerization system. For example, the first product via line 174 is sufficiently high in light components, including in this case nitrogen at about 83.1 wt % and sufficiently low in heavy components (e.g., butene at <0.005 wt % and iso-pentane at <0.005 wt %) that the first product can be used as the purge gas via line 112 for purging the polymer product. In another example, the second product via line 178 is sufficiently high in light hydrocarbons (ethylene at about 51.4 wt % and ethane at about 16.2 wt %) that the second product via line 178 can be recycled back to the polymerization reactor 103, thereby recycling monomer (ethylene) and comonomer (butene) thereto. Additionally, since the second product via line 178 is at a pressure of about 2,760 kPa, the second product via line 178 can be recycled directly to the polymerization reactor 103 that is operated at a pressure of about 2,515 kPa without additional compression. In another example, the third product in line 185 contains about 52.3 wt % ethylene and about 16.3 wt % ethane. As such, at least a portion of the third product in line 185 can be recycle via line 186 to the purge gas product in line 116, which can increase the concentration of the lighter components, e.g., ethylene and ethane, in the compressed purge gas product in line 149 to maintain a desired level of refrigerant within the auto-refrigeration system 160.

All numerical values are "about" or "approximately" the indicated value, and take into account experimental error and variations that would be expected by a person having ordinary skill in the art. All pressure values refer to absolute pressure unless otherwise indicated.

Various terms have been defined above. To the extent a term used in a claim is not defined above, it should be given the broadest definition persons in the pertinent art have given that term as reflected in at least one printed publication or issued patent. Furthermore, all patents, test procedures, and other documents cited in this application are fully incorporated by reference to the extent such disclosure is not inconsistent with this application and for all jurisdictions in which such incorporation is permitted.

While the foregoing is directed to embodiments of the present invention, other and further embodiments of the invention may be devised without departing from the basic scope thereof, and the scope thereof is determined by the claims that follow.

What is claimed is:

1. A method for recovering hydrocarbons from a polyolefin purge gas product, comprising:
   recovering a polyolefin product comprising one or more volatile hydrocarbons from a polymerization reactor;
   contacting the polyolefin product with a purge gas to remove at least a portion of the volatile hydrocarbons to produce a polymer product having a reduced concentration of volatile hydrocarbons and a purge gas product enriched in volatile hydrocarbons, wherein the volatile hydrocarbons comprise hydrogen, methane, one or more $C_2$-$C_{12}$ hydrocarbons, or any combination thereof, and wherein the purge gas product is at a pressure of about 101 kPaa to about 300 kPaa;
   compressing the purge gas product to a pressure of about 2,500 kPaa to about 10,000 kPaa;
   cooling the compressed purge gas product;
   separating the cooled purge gas product into at least a first product, a second product, and a third product, wherein heat is transferred from the compressed purge gas product to the first product, the second product, and the third product; and
   recycling at least a portion of at least one of the first product as the purge gas, the second product to the polymerization reactor, or the third product to the purge gas product enriched in volatile hydrocarbons prior to compression.

2. The method according to claim 1, wherein the purge gas product is compressed in two stages, wherein the first stage compresses the purge gas product at a pressure ratio of from about 1:6 to about 1:10, and wherein the second stage compresses the purge gas product at a pressure ratio of from about 1:3 to about 1:6.

3. The method according to claim 1, wherein compressing the purge gas product comprises serially compressing the purge gas product in two or more compression stages, and wherein the compressed purge gas recovered from each compression stage is cooled and at least a portion of any condensed liquid is separated from each compressed purge gas after each compression stage to produce a condensed product and a gaseous compressed product.

4. The method according to claim 3, further comprising recycling at least a portion of the one or more condensed products to the polymerization reactor.

5. The method according to claim 1, wherein cooling the compressed purge gas product comprises introducing the compressed purge gas product to an refrigeration system, wherein at least a portion of the compressed purge gas product is used as a refrigerant in the refrigeration system.

6. The method according to claim 5, wherein cooling the compressed purge gas product further comprises expanding the three products and indirectly transferring heat from the compressed purge gas product to the three products.

7. The method according to claim 1, wherein the compressed purge gas product is at a pressure of about 3,100 kPaa to about 4,500 kPaa.

8. The method according to claim 1, wherein the compressed purge gas product is cooled to a temperature of less than about −65° C.

9. The method according to claim 1, wherein a temperature of the purge gas product is maintained below a predetermined maximum temperature during compression, wherein the predetermined maximum temperature is less than about 200° C.

10. The method according to claim 1, wherein the purge gas comprises nitrogen, and wherein the first product comprises about 70 wt % or more nitrogen.

11. The method according to claim 1, wherein the first product comprises less than about 500 ppmv $C_4$ hydrocarbons, less than about 250 ppmv $C_5$ hydrocarbons, less than about 100 ppmv $C_6$ hydrocarbons, and less than about 100 ppmv $C_7$ and heavier hydrocarbons.

12. A system for recovering hydrocarbons from a polyolefin purge gas product, compromising:
   a purge bin adapted to receive a polyolefin product comprising one or more volatile hydrocarbons from a polymerization reactor, wherein the polyolefin product is contacted with a purge gas within the purge bin to remove at least a portion of the volatile hydrocarbons to produce a polyolefin product having a reduced concentration of volatile hydrocarbons and a purge gas product enriched in volatile hydrocarbons, wherein the volatile hydrocarbons comprise hydrogen, methane, one or more $C_2$-$C_{12}$ hydrocarbons, or any combination thereof, and wherein the purge gas product is at a pressure of about 101 kPaa to about 300 kPaa;
   a compression system adapted to compress the purge gas product to a pressure of about 2,500 kPaa to about 10,000 kPaa;
   a refrigeration system adapted to cool and separate the compressed purge gas product into a first product, a second product, and a third product, wherein heat is transferred from the compressed purge gas product to the first product, the second product, and the third product; and
   at least one recycle line adapted to recycle at least a portion of at least one of the first product as the purge gas, the second product to the polymerization reactor, and the third product to the purge gas product enriched in volatile hydrocarbons prior to compression.

13. The system according to claim 12, further comprising a recycle line adapted to recycle at least a portion of the compressed purge gas product to the purge gas product prior to compression.

14. The system according to claim 12, wherein the compression system comprises at least two compressors.

15. The system according to claim 14, wherein the compression system further comprises at least one recycle line adapted to recycle a portion of the compressed purge gas after compression in at least one of the compressors upstream of the compressor.

16. The system according to claim 12, wherein the compression system comprises two or more compressors, one or more heat exchangers adapted to cool the compressed purge gas recovered from each compressor, and one or more separators adapted to separate at least a portion of any condensed fluid from the compressed purge gas product after each compressor.

17. The system according to claim 12, wherein the refrigeration system comprises one or more heat exchangers adapted to cool the compressed purge gas by indirectly exchanging heat from the compressed purge gas to three or more products produced within the refrigeration system, and wherein each of the three or more products comprise a portion of the compressed purge gas after cooling.

18. The system according to claim 12, wherein the refrigeration system is adapted to use the compressed purge gas product as a source of a refrigerant in the refrigeration system.

19. A method for recovering hydrocarbons from a polyolefin purge gas product, comprising:
- recovering a polyolefin product comprising one or more volatile hydrocarbons from a polymerization reactor;
- contacting the polyolefin product with a purge gas to remove at least a portion of the volatile hydrocarbons to produce a polymer product having a reduced concentration of volatile hydrocarbons and a purge gas product enriched in volatile hydrocarbons, wherein the volatile hydrocarbons comprise hydrogen, methane, one or more $C_2$-$C_{12}$ hydrocarbons, or any combination thereof, and wherein the purge gas product is at a pressure of about 40 kPaa to about 100 kPaa;
- compressing the purge gas product to a pressure of about 2,500 kPaa to about 10,000 kPaa;
- cooling the compressed purge gas product;
- separating the cooled purge gas product into at least a first product, a second product, and a third product, wherein heat is transferred from the compressed purge gas product to the first product, the second product, and the third product; and
- recycling at least a portion of at least one of the first product as the purge gas, the second product to the polymerization reactor, or the third product to the purge gas product enriched in volatile hydrocarbons prior to compression.

20. A system for recovering hydrocarbons from a polyolefin purge gas product, compromising:
- a purge bin adapted to receive a polyolefin product comprising one or more volatile hydrocarbons from a polymerization reactor, wherein the polyolefin product is contacted with a purge gas within the purge bin to remove at least a portion of the volatile hydrocarbons to produce a polyolefin product having a reduced concentration of volatile hydrocarbons and a purge gas product enriched in volatile hydrocarbons, wherein the volatile hydrocarbons comprise hydrogen, methane, one or more $C_2$-$C_{12}$ hydrocarbons, or any combination thereof, and wherein the purge gas product is at a pressure of about 40 kPaa to about 100 kPaa;
- a compression system adapted to compress the purge gas product to a pressure of about 2,500 kPaa to about 10,000 kPaa;
- a refrigeration system adapted to cool and separate the compressed purge gas product into a first product, a second product, and a third product, wherein heat is transferred from the compressed purge gas product to the first product, the second product, and the third product; and
- at least one recycle line adapted to recycle at least a portion of at least one of the first product as the purge gas, the second product to the polymerization reactor, and the third product to the purge gas product enriched in volatile hydrocarbons prior to compression.

* * * * *